(12) United States Patent
Ke

(10) Patent No.: US 7,951,585 B2
(45) Date of Patent: May 31, 2011

(54) CONSTRUCTION OF ONCOLYTIC ADENOVIRUS RECOMBINANT SPECIFICALLY EXPRESSING IMMUNE MODULATORY FACTOR GM-CSF IN TUMOR CELLS AND USES THEREOF

(75) Inventor: Zunhong Ke, Chengdu (CN)

(73) Assignee: Chengdu Kanghong Biotechnologies Co., Ltd., Chengdu, Sichuan (CN)

( * ) Notice: Subject to any disclaimer, the term of this patent is extended or adjusted under 35 U.S.C. 154(b) by 1133 days.

(21) Appl. No.: 11/628,760

(22) PCT Filed: Nov. 19, 2004

(86) PCT No.: PCT/CN2004/001321
§ 371 (c)(1), (2), (4) Date: Dec. 7, 2006

(87) PCT Pub. No.: WO2005/121343
PCT Pub. Date: Dec. 22, 2005

(65) Prior Publication Data
US 2010/0047208 A1    Feb. 25, 2010

(30) Foreign Application Priority Data

Jun. 7, 2004   (CN) .......................... 2004 1 0046237

(51) Int. Cl.
*C12N 15/00*   (2006.01)
*A61K 35/76*   (2006.01)

(52) U.S. Cl. ................................... 435/320.1; 424/93.2
(58) Field of Classification Search ................. 536/24.1; 424/93.2; 435/325
See application file for complete search history.

(56) References Cited

U.S. PATENT DOCUMENTS

| | | | |
|---|---|---|---|
| 5,891,432 A * | 4/1999 | Hoo | 424/93.21 |
| 6,020,191 A | 2/2000 | Scaria et al. | |
| 6,348,450 B1 | 2/2002 | Tang et al. | |
| 6,627,190 B2 | 9/2003 | Wold et al. | |
| 7,592,317 B1 * | 9/2009 | Weichselbaum et al. | 514/44 R |
| 2003/0099616 A1 * | 5/2003 | Irving et al. | 424/93.2 |
| 2005/0181507 A1 * | 8/2005 | Havenga et al. | 435/456 |

FOREIGN PATENT DOCUMENTS

| | | |
|---|---|---|
| CN | 1381582 A | 11/2002 |
| WO | 96/09399 A2 | 3/1996 |

OTHER PUBLICATIONS

Kawashima et al. Clin Cancer Research 10:285-292, Jan. 2004.*
Alignment printout. p. 1 dated May 7, 2010.*

* cited by examiner

*Primary Examiner* — Deborah Crouch
*Assistant Examiner* — Marcia S Noble
(74) *Attorney, Agent, or Firm* — The Nath Law Group; Susanne M. Hopkins; Charles D. Niebylski

(57) ABSTRACT

The present invention relates to gene therapy for tumors, specifically, it relates to the construction of oncolytic adenovirus recombinant, which specifically expresses immune modulatory factor GM-CSF in tumor cells and uses thereof.

20 Claims, 11 Drawing Sheets

```
-167
CTAGCCCCACGTGGCGGAGGGACTGGGGACCCGGGCACCCGTCCTGCCCCTTCACCTTCCAGCTCCGCCTCCTCCGCGCG
     E-box                                                          Sp1
     Myc/MAX/USF GACCCCGCCCCGTCCCGACCCCTCCCGGGTCCCCGGCCCAGCCCCCTCCGGGCCCTCCCAGCCCCTCCCCTTCCTTTCCGC
     GC-box                         Sp1                Sp1

+1
GGCCCCGCCCTCTCCTCGCGGCGCGAGTTTCAGGCAGCGCTGCGTCCTGCTGCGCACGTGGGAAGCCCTGGCCCCGGCC
     Sp1                                              E-box              NF-1
                                                      Myc/MAX/USF

ACCCCCGCGATG
```

(SEQ ID NO: 1)

Fig. 1

(SEQ ID NO: 2)

CONSTRUCTION OF ONCOLYTIC ADENOVIRUS RECOMBINANT SPECIFICALLY EXPRESSING IMMUNE MODULATORY FACTOR GM-CSF IN TUMOR CELLS AND USES THEREOF

This is a National Phase Application filed under 35 U.S.C. §371 as a national stage of PCT/CN2004/001321, filed on Nov. 19, 2004, an application claiming the benefit under 35 U.S.C. §119 of Chinese Patent Application No. 200410046237.X, filed Jun. 7, 2004, the content of each of which is hereby incorporated by reference in its entirety.

FIELD OF THE INVENTION

The present invention relates to a gene therapy for tumors; More specifically, it relates to a construction of oncolytic adenovirus recombinants, which preferentially replicates in tumor cells and expresses immune-stimulating factor to induce tumor-specific immune response in human body.

BACKGROUND OF INVENTION

It has been more than a century since a virus was used to treat neoplastic disease. Doctors noticed that occasionally a patient was cured after a virus infection. This puzzle was not resolved until the beginning of 1920s and since then attracted attentions from scientists and clinical doctors. That was the beginning of the virotherapy (using viruses to treat cancer). By 1950s, more than 50 viruses had been tested for anti-tumor activity in animals or patients (Mullen and Tanabe (2002) *The Oncologist* 7:106-119; McCormick F (2001) *Nature Review Cancer* 1:130-141). In 1956, Dr. Smith and his team treated more than 30 cervical cancer patients with lysate of HeLa cells or KB cells that were infected with 10 serotypes of wild-type adenoviruses through intratumor injection, intra-hepatic arterial injection or intravenous injection. No severe side effects were observed except the flu symposium in most patients; on the other hand, tumors of several patients went shrinkage and were necrotic. Unfortunately, due to the limitation of virus production band purification, this work did not proceed further. Dr. Smith's work had encouraged many scientists to explore the possibility of using viruses to treat cancers (Chiocca E A (2002) *Nature Review Cancer* 2: 938-950).

Along with the progress made in molecular biology and genetic engineering, in particular, with better understandings into viruses in relation to human being, scientists have been enabled to genetically manipulate viral genome since late last century, which includes the success of creating virus mutants that can specifically replicate in tumor cells (McCormick F (2001) *Nature Review Cancer* 1:130-141). For example, glioma-specific herpes virus mutant G207 (Martuza et al., (1991) *Science* 252:854-856), adenovirus Addl1520 (Onyx-015), an adenovirus mutant preferentially replicating in p53 defective tumor cells (Bischoff et al., (1996) *Science* 274: 373-376) and CV706, a prostate cancer cell specific adenovirus mutant (Rodriguez et al. (1997) *Cancer Research* 57:2559-2563). This work has laid a foundation for the formation of new field: Cancer Virotherapy. At present, there are over 20 virus variants in clinical trials (Mullen and Tanabe (2002) *The Oncologist* 7:106-119).

There are several approaches for making tumor cell-specific oncolytic viruses. One approach to make a virus variant that selectively replicates in tumor cells is to use tumor cell-specific regulatory elements such as promoters and enhancers to control expression of essential viral genes, for example, the E1A, E1B, E2 and E4 genes of adenovirus (DeWeese et al. (2001) *Cancer Research* 61:7464-7472). By this approach, essential viral genes and ultimately virus replication would be under the control of tumor cell-specific regulatory elements, such regulatory elements include prostate-specific antigen (PSA) promoter and enhancers, alpha-feto protein (AFP) promoter and enhancers, human E2F-1 promoter etc. (McCormick F (2001) *Nature Review Cancer* 1:130-14).

Telomerase is an important enzyme for controlling length of cells' chromosome end, capable of regulating the length of the chromosome end during the process of cell fission. Telomerase is consisted mainly of the three parts, wherein RNA and telomerase reverse transcriptase gene (hTERT), which is of catalytic activity, control the activity of telomerase, while hTERT promoter determines the expression and activity of the telomerase.

Further researches have indicated that telomerase has no or very low activity in adult's normal cells. (Kim N W et al. *Science.* Dec. 23, 1994; 266(5193):2011-5; Shay J W et al. *European Journal of Cancer* 1997, 33;271-282), while it has a high delivery level in more than 90% tumor cells (Hahn and Weinberg (2002) *Nature Review Cancer* 2:331-341; Shay and Wright (1996) *Current Opinion Oncology* 8:66-71). Based on these features of hTERT, scientists have successfully generated several vectors in which the hTERT promoter was incorporated into the viral genome for gene delivery, including the works recently published describing the use of the hTERT promoter for conditionally replicating oncolytic adenoviruses (Lanson et al. (2003) *Cancer Research* 63:7936-7941; Kawashima et al., (2004) *Clinical Cancer Research* 10:285-292; Kim et al. (2003) *Oncogene* 22:370-380; Irving et al. (2004) *Cancer Gene Therapy* 11:174-185).

There are a few endogenous regulatory elements in adenoviral genome, which regulates expression of viral genes, for example, the promoter and enhancer of the E1A gene, among these endogenous regulatory elements, the sequence of the E1A enhancer overlaps with the viral packaging signal. In order to minimize the impact of endogenous regulatory elements on the regulation of a heterologous promoter, scientists had relocated the packaging signal to the right arm from the native site at the left end (Bristol et al. (2003) *Molecular Therapy* 7(6):755-764; Jakubczak et al. (2003) *Cancer Research* 63:1490-1499). Unfortunately, this kind of relocation of viral packaging signal from the native site to the right end has destabilized viral genome, resulting in the generation of many viral mutants (WO 02/067861; *ASGT* 2003 *Annual Meeting, Molecular Therapy*). Therefore, the above said relocation of viral packaging signal is not a viable approach to minimize the impact of endogenous regulatory elements. How to minimize the impact of the endogenous viral regulators on the heterologous elements and to prevent undesired generation of many viral mutants, while keep the viral genome stable?

With respect to the expression level of telomerase in humans, during the embryonic development and differentiation, scientists have also come to recognize that there is a certain level of telomerase activity in some cells including cervical member cells, progenitors, and stem cells (Wright et al. (1996) *Development Genetics* 18:173-179; Sharma et al. (1995) *Proc. Natl. Acad. Sci. USA* 92:12343-12346; Kolquist et al. (1996) *British Journal of Cancer* 80:1156-1161; Tahara et al. (1999) *Oncogene* 18:1561-1567; Tanaka et al. (1998) *American Journal of Pathology* 153:1985-1991). Low level of telomerase expression activity has cautioned scientists when they used the hTERT promoter to deliver a therapeutic gene in gene therapy vector, or to generate tumor cell-specific oncolytic adenoviruses by controlling essential viral genes (Hahn WC (2004) *Clinical Cancer Research* 10:1203-1205). Due to low level of telomerase expression in non-targeting cells, such as the progenitors, the hTERT promoter controlling oncolytic adenoviruses may replicate massively in progenitor cells, resulting in severe side effects (Huang et al. (2004) *Clinical Cancer Research* 10:1439-1445; Hahn WC (2004) *Clinical Cancer Research* 10:1203-1205; Masutomi et al. (2003) *Cell* 114:241-253). Therefore, increasing tumor cell specificity of the hTERT promoter is one of the key projects in generating oncolytic adenovirus using the hTERT promoter.

SUMMARY OF INVENTION

In one aspect, the present invention provides a recombinant for control ling expression of essential viral genes of human adenovirus, the recombinant is obtained by incorporating tumor cell-specific regulatory elements into the adenovirus.

To accomplish this invention, in another aspect, the present invention provides tumor cell-specific oncolytic adenoviruses as well as recombinants ontainable by combining the oncolytic adenovirus with immune regulatory element via genetically engineering method, The recombinant is constructed by incorporating the tumor cell-specific promoter and the immune regulatory gene into the adenovirus genome via DNA clonical technology, thereby obtained is a fused sequence capable of replicating in the tumor cells and expressing the immune regulatiory gene in the tumor cells.

In another aspect, this invention provides a tumor cell-specific oncolytic virus recombinant capable of expressing immune-stimulating factor. This recombinant consists mainly of essential viral vector, tumor cell-selective regulatory element and an immune-stimulating factor.

In another aspect, this invention provides a method of generating a conditionally replicating oncolytic virus recombinant.

In another aspect, this invention provides an use of the conditionally replicating oncolytic virus recombinant in manufacture of a medicament for prevention and/or therapeutic treatment of cancers.

In another aspect, this invention provides a medicament for prevention and/or therapeutic treatment of cancers which contains therein the conditionally replicating oncolytic virus recombinant.

In another aspect, this invention provides a promoter of the nucleotide sequence indicated in the SEQ ID NO. 2.

The recombinant according to the present invention can be used to control the adenoviruses to such an extent that these adenovirus replicate only in the tumor cells. By modifying genetically the hTERT promoter, the recombinant of the invention has a substantially enhanced the specificity of the hTERT promoter to the tumor cells.

The method of preparing the oncolytic virus recombinant having a tumor cell-specificity, according to the invention, comprises the step of incorporating by genetically engineering an immune-stimulating factor gene, which is capable of inducing a specific immune-stimulating response of human body to the tumor cells, with the tumor cells-specific replicating viral genome. The resulted virus recombinant can selectively replicates in a specific cell population and can replicate and propagate in tumor cells, and therefore kill the tumor cells, thus the recombinant can be used to treat cancer and prevent tumor.

This invention also provides a novel method of propagating the conditionally replicating oncolytic adenovirus recombinant over the ones known from the prior art. In the prior art, the construction and propagation of conditionally replicating oncolytic adenovirus recombinant or genetically engineered viral vectors is in a genetically engineered cell lines, such as cell line 293. Such a cell line expresses adenoviral E1 proteins to complement the function of replication-defective E1-deleted adenoviral vector or a conditionally replicating oncolytic adenovirus recombinant in which viral E1 gene is under the control of a tumor cell-selective regulatory element. Unfortunately, the recombinant produced in such a cell line usually contains a certain amount of wild-type or recombined adenovirus (referred to as replication-competent adenovirus, RCA). The reason for the generation of RCA in the recombinant product is that in the generation cells such as the kind of cell line 293 there contains the gene sequence of the adenovirus; this piece of "wild-type" adenovirus sequence will recombine in the cell with the E1-deleted or E1-improved adenovirus, resulting either a "wild-type" adenovirus or a recombinant adenovirus. Such a product may not meet the product specifications and may cause unexpected side effect with safety concens. The cell used for construction of the recombinant according to the invention contains no adenoviral gene sequence and therefore can avoid the RCA and resolve the safety problem as mentioned above.

This invention provides a conditionally replicating oncolytic adenovirus recombinant in which the capsid protein has been improved to increase the binding affinity of the recombinant to tumor cells, resulting in an increase in infectivity of the recombinant to tumor cell. Many recent studies have demonstrated a low or no expression of adenovirus receptor 5 (the coxsackie virus B and adenovirus receptor, CAR) in tumor cells, however, all tumor cells express a high level of CD46 (Shayakhmetov et al., 2002. Cancer Research 62:1063-1068). Further studies have shown that the receptor for Adenovirus serotype 35 is CD46 protein molecule (Sirena et al. (2004) Journal of Virology 78(9):4454-4462). Therefore, we propose to replace the fiber knob of the protein sequence in the adenovirus serotype 5 virus recombinant with that of adenovirus serotype 35, the later is capable of binding the CD46 protein receptor, so as to construct a recombinant which has a fused adenovirus capable of binding the receptor. It is believed that such a recombinant will have better infectivity in a wider spectrum of tumor cells.

The conditionally replicating oncolytic virus according to the invention can be a DNA virus or a RNA virus, can be any one of adenovirus serotypes including serotype 5, 2, 35, 41, etc., preferably serotype 5 or an improved adenovirus. For example, an adenovirus recombinant in which the E1A gene and the E1B gene are linked together by internal ribosome entry site (IRES); an adenovirus recombinant in which the fiber knob of adenovirus type 5 is replaced with that of adenovirus serotype 35; an adenovirus recombinant in which a transcription terminal sequence is inserted downstream of viral ITR and the packaging site and upstream of the a heterologous promoter such as hTERT promoter; the adenovirus with its encoding sequence for 10.4K, 14.5K and 14.7K in the E3 region being deleted. The said transcription terminal sequence can terminate gene transcription mediated by any RNA polymerase, such as SV40 early poly (A) singal sequence; such as the adenovirus recombinant with its sequences for encoding 10.4K, 14.5K and 14.7K in the E3 fragment being deleted.

The said gene regulatory element that is tumor cell-specific is any of promoter, enhancer, silencer or their combination, preferabley the improved hTERT promoter as indicated in the SEQ. ID No. 2, and this promoter has binding site for transcription factor E2F-1.

The said immune regulatory element can be any gene or their variants that can stimulate and induce immune response, such as IL-2, IL-10, IL-12, IL-15, IL-24, IL-25, GM-CSF, G-CSF and INF-alpha, INF-beta, etc, preferable GM-CSF, including its secreted and membrane-bound forms as well as their variants.

A preferable adenovirus recombinant according to the invention is such a recombinant, in which the essential virus vector is such an improved adenovirus that, in the adenovirus sequence, a transcription terminal sequence is inserted downstream of the viral ITR and the packaging site but upstream of the heterologous promoter, and the tumor cell-specific regulatory element is the hTERT promoter with its sequence shown in SEQ ID NO. 2, the immune-stimulating gene is GM-CSF having a sequence shown in SEQ ID NO. 3 (KH-901) or being in a membrane-bound GM-CSF (KH-902).

Another preferable adenovirus recombinant according to the invention is such one, wherein the essential virus vector is such an improved adenovirus that, in its sequence, the fiber knob is from adenovirus serotype 35 in replacement of that of adenovirus serotype 5, and the tumor cell-specific regulatory element is the hTERT promoter having the sequence shown in SEQ ID NO. 2, and the immune-stimulating gene is GM-CSF (KH-904), preferably a membrane-bound GM-CSF (KH-905).

The E1A gene and the E1B gene is linked by IRES, the fiber knob is from serotype 35, a transcription terminal element is inserted downstream of the ITR and the packaging site and upstream of a heterologous regulatory element; the tumor selective regulatory element is the hTERT promoter with sequence of SEQ ID NO. 2, in which the immune stimulating gene is GM-CSF, preferably in its membrane bound form.

Another preferable adenovirus recombinant according to the invention is such one, wherein the essential virus vector is such an improved adenovirus that, in the adenovirus sequence, a transcription terminal sequence is inserted downstream of the viral ITR and the packaging site but upstream of the heterologous promoter; the adenovirus with its encoding sequence for 10.4K, 14.5K and 14.7K in the E3 region being deleted; the tumor cell-specific regulatory element is the hTERT promoter having the sequence shown in SEQ ID NO. 2, the tumor-stimulating gene is GM-CSF, preferably the membrane-bound GM-CSF (KH-903).

Another preferable adenovirus recombinant according to the invention is such one, in whch a transcription terminal sequence is inserted downstream of viral ITR and the packaging site and upstream of the heterologous promoter, and the adenoviral E1A gene and the E1B gene are linked by IRES, the tumor cell-specific regulatory element is the hTERT promoter having the sequence shown in SEQ ID NO. 2, and the immune-stimulating gene is GM-CSF (KH-906).

The adenovirus recombinants according to the invention include but not limit to KH-901, KH-902, KH-903, KH-904, KH-905 and KH-906, in which the sequence for KH-901 is shown in SEQ ID NO. 3, wherein, 1) 1-103: adenoviral left ITR {adenovirus serotype 5 of sequence shown in Genbank No. BK000408};

2) 194-358: adenovirus packaging sequence and the enhancing sequence for E1;

3) 362-534: SV40 poly(A) signal sequence and the linker (the sequence of adenovirus serotype 5 from which np 362 to 551 have been deleted);

4) 525-811: the sequence of the genetically improved hTERT promoter and the linker;

5) 812 to the right: adenovirus sequence including E1A, E1B, E2, etc.;

6) 28995-29436: immune-stimulating GM-CSF gene;

7) 29437 to the right: adenovirus sequence of E4 gene and the right end;

The sequence of KH-900 is similar to the sequence shown in SEQ ID NO. 3, while its sequence of the hTERT promoter is in wild-type without base transversion (please ferer to SEQ ID NO. 1 and 2).There is no SV40 poly(A) signal sequence between the packaging site and the hTERT promoter.

The sequence of KH-902 is similar to KH-901, but the immune-stimulaitng gene GM-CSF is replaced by its membrane-bound form with the sequence shown in SEQ ID NO. 4.

The sequence of KH-903 is similar to KH-901, except that the encoding sequence for 10.4 Km 14.5K and 14.7K has been deleted, the deleted sequence is the part of the adenoviral genome from np 29804 to 30857. The proteins from these enconding sequences inhibit immune response, particularly the tumor necrosis factor (TNF)-mediated immune response. Therefore, the deletion of these encoding regions will enhance the tumor-targeted immune responses induced by the conditionally replicating oncolytic adenoviruses.

The sequence of KH-904 is similar to KH-901, except that the fiber knob is changed from adenovirus serotype 5 to serotype 35, the sequence is shown in SEQ ID NO. 5. Late research has revealed that many tumor cells do not express the receptor protein CAR of the adenovirus serotype 5, but express at a high level of CD46 molecule. CD46 molecule is the receptor for adenovirus serotype 35. Therefore the presence of fiber knob from adenovirus serotype 35 will enhance the infectivity of the conditionally replicating oncolytic adenovirus recombinants.

KH-905 is similar to KH-904 except that the immune-stimulating gene GM-CSF has been changed from secreted form to membrane bound form.

KH-906 is made from KH-901 by replacing the endogenous E1B promoter with an internal ribosome entry site (Li et al., (2001) Cancer Research 62; Zhang et al. (2002) Cancer Research 62:3743-3750).

This invention also provides the sequence of the improved hTERT promoter as shown in SEQ ID NO. 2, this promoter has binding site for transcription factor E2F-1.

This invention also provides a method of generating the above said improved hTERT promoter. Two primers were synthesized based on the sequence of the hTERT promoter as shown in FIG. 1:

A. 5'-GTCTGGATCCGCTAGCCCCACG-3'

B. 5'-CGACCGGTGATATCGTTTAATTCGC-3'

The hTERT promoter was amplified by PCR with activated human genomic DNA as the template, and primers were shown above. The condition for the PCR reaction is as follow: for the first cycle, 94° C. for 5 minutes for denature, 81° C. for 1 minute for annealing, 72° C. for 2 minutes for extention; For each of the following 35 cycles: 93° C. for 1 minute for denature, 68° C. for 1 minute for annealing, 72° for 2 minutes for extention. The PCR product was analyzed in agar gel and the hTERT promoter fragment was recovered for confirmation by sequencing. The sequence was confirmed as published (FIG. 1). The DNA of the purified PCR fragment was cloned into the pUC19 vector. With mutagenesis method described by Strategene (site-directed mutagenesis), the sequence of the hTERT promoter was changed to that as shown in FIG. 2.

This invention thus also provides the improved hTERT promoter with the sequence as shown in SEQ ID NO. 2, which can be obtained by the above said method.

In the hTERT promoter according to the invention, there is no TATA conserved basepairs, but there are two sequences like E box of CACGTG and 4 GC-rich Sp-I binding regions. These conservative sequences are crucial for expression of the telomerase, as the transcription of the telomerase is regulated by the hTERT promoter through C-Myc/Max and Sp-I (Cong et al (1999) Human Molecular Genetics 8(1):137-142; Kyo et al (2000) Nucleic Acids Research 28(3):669-677). Many studies have revealed that Myc plays an important role in cell proliferation and cell cyling, therefore the above said modification of the hTERT promoter will further impact the transcription and expression of the telomerase.

In order to minimize the activity of the hTERT promoter in normal cells such as progenitor and to increase its tumor cell-selectivity, we have analyzed in detail the binding sites of the transcription factor in the hTERT promoter through computer modeling. Based on the computer modeling, we made analysis on a series of mutagenesis, among them, we identified one mutant in which the fourth Sp-I had been changed to the E2F-1 binding site, the sequence had been changed from ' . . . TTTCCGCGGCCCCGGCC . . . ' (FIG. 1) to ' . . . TTTCCGCGGCAACGCCC . . . ' (FIG. 2).

In vitro study showed that the improved hTERT promoter maintains the activity in tumor cells and significantly reduces the "promoting" activity in normal cells. Therefore, the improved promoter has a significantly reduced transcription activity in normal cells including progenitor cells. It was demonstrated in transient transfection experiment using reported gene that, in the tumor cells, the improved hTERT promoter has an activity about 5 to 10 times higher than that of the wild-type hTERT promoter, while in normal cells, the improved hTERT promoter has a much reduced activity (FIG. 6). We then constructed a conditionally replicating oncolytic adenovirus by controlling essential viral gene with the improved hTERT promoter, the resulted oncolytic virus is not toxici to stem cells (FIG. 7); thus the resulted oncolytic adenovirus has a significantly improved safety for clinical application.

As the E2F-1 promoter is active in the tumor cells defective in the pRb/E2F/p16 pathway, it has been widely used in gene therapy, particular in the construction of conditionally replicating oncolytic adenovirus (Parr et al. (1997) Nature Medicine 3(10):1145-1149; Jakubczak et al. (2003) Cancer Research 63:1490-1499; Bristol et al. (2003) Molecule Therapy 7(6):755-763). The improved hTERT promoter has not only binding sites for the transcription factors E2F-1, but also binding sites Sp-I and NF-1 that are possessed in E2F-1 promoter, thus the improved hTERT promoter is active in tumor cells that are up-regulated telomerae and defective in the Rb pathway. Therefore, the improved hTERT promoter is active in these two kinds of tumor cells, but not active in normal cells such as stem cells; this represents a high tumor specificity.

In the meanwhile, this invention provides a conditionally replicating oncolytic adenovirus recombinant in which the E1A gene and the E1B gene are linked by internal ribosome entry site (IRES) and thus brings the transcription of the two important genes E1A and E1B of the adenovirus recombinant under the control of the improved hTERT promoter such as KH-906.

This invention provides an oncolytic adenovirus recombinant in which a transcription termination signal is placed downstream of the ITR and the viral packaging site and upstream of the tumor cell-specific promoter such as the hTERT promoter. The transcription termination signal such as SV40 early poly(A) can block any RNA polymerase-mediated transcription. In vitro studies have demonstrated that, owing to the presence of the transcription termination signal such as SV40 early poly(A), the ITR and the sequence, which overlaps in the packaging site and has an effect as an enhancer, has only minor impact on the hTERT promoter.

The oncolytic adenovirus recombinants according to the invention have immune-stimulating genes. In several known oncolytic adenovirus recombinants, the GM-CSF gene was used as immune-stimulating gene, the oncolytic adenovirus recombinants described in this invention also contain the GM-CSF gene as immune-stimulating gene, though not being limited to the GM-CSF gene, and other immune-stimulating genes such as cytokine could also be used. However, GM-CSF is well known to be an inducer for long lasting immune responses (Dranoff et al. (1993) Proc. Natl. Acad. Sci. USA 90:3539-3543). It is a secreted glycoprotein that can stimulate differentiation of granulocytes, monocytes, macrophage and dendritic cells, and increase expression of MHC and B7 co-stimulating molecule on the antigen-presenting cells. GM-CSF can also enhance the infiltration of immune cells into tissues and the differentiation of B cells. Due to the property of GM-CSF described above, scientists have used in the past years GM-CSF in combination with chemotherapy for treating cancers. Many tumor vaccines consisting of tumor cells capable of expressing GM-CSF are currently in clinical trials (Armitage (1998) Blood 92:4491-4508; Mach et al. (2000) Cancer Research 60:3239-3246; Gilboa (2004) Nature Reviews Cancer 4:401-411). A conditionally replicating oncolytic adenovirus that expresses GM-CSF can not only kill cancer cells but also express GM-CSF in tumor cells to induce tumor cell-specific immune responses, resulting in cancer immunotherapy effects. Therefore this process of establishing autologous tumor vaccine has not only eliminated the complicated process of preparing tumor vaccine, but also maintains the high integrity of tumor cells without in vitro manipulation, including antigen expression, which has made the cancer vaccine in situ more effective. Therefore oncolytic virus described above can kill tumor cells at the site where the virus is delivered and at the same time will also kill distant tumor cells through GM-CSf mediated immune responses. The method of the invention described here is an unique approach of making better oncolytic viruses.

Two oncolytic adenovirus recombinants, among the ones according to the invention, contain and express the membrane-bound GM-CSF (mbGM-CSF). Previous studies have revealed that membrane-bound GM-CSF can enhance the interaction with dendritic cells and induce better immune responses than the secreted GM-CSF (Soo Hoo et al. (1999) Journal of Immunology 169:7343-7349; Yei et al. (2002) Gene Therapy 6:1302-13 11). It has not been reported that membrane-bound GM-CSF is expressed in a conditionally replicating oncolytic adenovirus recombinant so as to obtain a genetically recombined active ingredient.

This invention also provides a method of making oncolytic virus recombinants, comprising the following steps:
  a) constructing the left arm of adenoviral genome that contains the hTERT promoter;
  b) constructing the right arm of adenoviral genome that contains an immune-stimulating gene;
  c) co-transfecting the plasmids containing the right arm and left arm of adenoviral genome into 293 cells, HeLa cells, HeLa-S3 cells or A549 cells, and the recombinant is generated through homologous recombinantion.

The recombinant of the invention can be obtained by the following process: the viral recombinant is made in mammalian cells thorugh homologous recombination. First of all, the endogenous promoter of the E1A gene is deleted from pXC.1 (a plasmid oontaining the left end of adenovirus serotype 5, purchased from Microbix, Canada) and replaced with SV40 poly(A) termination signal and the improved hTERT promoter through common cloning techniques, resulting in pKH-901a. In the meanwhile, the gp19K encoding sequence in pBHGE3 (a plasmid containing the right portion of adenovirus, purchased from Microbix, Canada) is replaced with the GM-CSF gene, resulting in a plasmid called pKH-901b.

Plasmid DNA of pKH-901a and pKH-901b is co-transfected into HeLa cells, a signle clone is picked up from plaquing and named to be KH-901. Following the same procedure, recombinants KH-900, KH-902, KH-903, KH-904, KH-905 and KH-906 were constructed.

As the matter of fact, the recombinants can be made in any mammalian or non-mammalian cells.

Following the plan outlined above, a DNA fragment from nucleotide was amplified by PCR at 362 to 551 of pXC.1 respectively with restriction endonucleases SspI and PinAI (AgeI). The hTERT promoter DNA fragment was amplified from human genomic DNA by PCR, linked to poly(A). Two restriction endonucleases SspI and PinAI were added to the two ends of the DNA fragment. The DNA fragment was digested with SspI and PinAI and ligated to pXC.1 that was digested with the same enzyme. The ligation was transformed into E.coli cells DH5-alpha cells (Invitro gene, USA), Ten colonies were picked up, cultured in an incubator for 24 hours. DNA was extracted and analyzed with restriction enzymes, the plasmid was confmed by sequencing and named as pKH-901a.

Using the primers of 5'-ATAACCATGTGGCTGC-3' and 5'-AAATTACTCCTGGACTGG-3', a DNA fragment encoding GM-CSF was amplified by PCR from the template cDNA extracted from activated macrophage. The full-legth GM-CSF gene was cloned into pUC19 and confirmed by sequencing. Subsequently, the cDNA fragment of the GM-CSF gene was cloned into pBHGE3 at the encoding region for gp19k, the resulted plasmid, named as KH902b, was sequenced and confirmed by restriction enzyme analysis.

Plasmid DNA of pKH-901a and pKH-901b were co-transfected into HeLa cells for homologous recombinantion. Before transfection, the plasmid DNA was linearized by ClaI and transfected into HeLA cells mediated by Lipofectin (USA Invitrogen), 10 days following the transfection, cells were harvested, 3 cycles of freeze/thaw, took 100 mL for plaquing on HeLa cells. Eight days following the plaquing, isolated plaques were visible under the agar 8 days following the plaquing. Six plaques were picked up, and inoculated in HeLa cells. Cell lysate was harvested 4 to 6 days following the inoculation. Adenoviral DNA was exfracted from cell lysate (Qiagen's kit), and the viral structure was confirmed through restriction enzyme digestion, PCR and Southern blot analysis. The resulted virus was named as KH-901.

The virus recombinant according to the invention can be used to prepare pharmaceutical composition for the treatment of cancers and/or for prevention of cancers. The virus recombinant can be used in combination with radiation and chemotherapy to complish better therapeutical efficacy.

The virus recombinant according to the invention can be formulated into injectable compositions for intravenous administration, intratumoral injection, intramuscular injection, subcutaneous injection, intra-organism injection, intrapelitoneal injection, etc.

For large-scaled preparation, the virus recombinant of the invention can be manufactured in HeLa cells, HeLa-S3 cells or A549 cells through cell culture, virus infection, propagation, concentration, purification. The virus recombinant manufactured through this process can be used as raw material to formulate into clinically injectable composition, together with pharmaceutically acceptable carriers by conventional formulation technology.

Experiments showing the potential application and favorable effects of the present invention are decribed as follows:

EXPERIMENT 1

Activity of the hETRT Promoter and Comparison of Tumor Cell-specificity Between the Wild-type and the Improved hTERT Promters To test the specificity of the improved version of the hTERT promoter, the wild-type hTERT promoter (telo) and the improved hTERT promoter (Mtelo) were linked to a report gene Luciferase (luc), the resulted plasmids were transfected into a panel of human cancer cells and human normal cells. The cells were harvested 48 hours following transfection and the cell lysates were used to determine the expression level of luciferase. During the transfection, a secondary report gene LacZ report plasmid was used to normalize the transfection efficicence among different types of cells. The result presented in FIG. 6 showed that (1) in the tumor cells, the improved promoter Mtelo showed much higher luciferase activity than the wild-type hTERT promoter (telo) did. For example, in Hep3B cells (up-regulated telomerase and Rb-pathway defective), Mtelo produced a luicifersae activity 6 times more than that of telo, and in LNCaP cells (up-regulated telomerase and Rb-pathway defective), Mtelo produced a luciferase activity 18 times more than that of the wild-type hTERT promoter; (2) in the human normal cells, the wild-type hTERT promoter telo led to a low level of transcription activity, while the improved hTERT promoter Mtelo had substantially a background level of transcription activity. For example, in MRC-5 cells (telomerase negative and Rb-pathway normal), the Mtelo promoter showed an activity 6 times less than that of the wild-type hTERT promoter telo. This result indicated that the addition of the E2F binding sites has significantly increased tumor cell-selectivity and transcription capability of the hTERT promoter.

This conclusion was further confirmed by the tests, wherein the improved selectivity of the improved hTERT promoter, the transcriptional activity of the promoter was determined in the cells infected with recombinants by measuring the number of E1A message copies. Four viruses were included in the study: wild-type adenovirus as positive control, replication-defective adenovirus dl312 (E1A deleted) as negative control, KH-900 (with the wild-type hTERT promoter) and KH-901 (with the improved hTERT promoter). Human foreskin keratinocytes (hFKs) and hFKs-E6, the hFK cells transformed with the E6 gene of the human papilloma virus type 16 (HPV-16) were used for the testing. hFKs-E6 was previously demonstrated to have up-regulated telomerase activity (Horikawa et al. (2001) Journal of Virology 75(9):4467-4472). Cells were infected with the viruses at a multiplicity of infection (MOI) of 1 plaque forming unit (pfu) per cell and the number of E1A message RNA was determined by reverse transcription PCR (RT-PCR). The result presented in FIG. 7 showed that no E1A message mRNA was detected in dl312 infected cells hFKs and hFKs-E6; approximately 4000 copies of E1A message RNA were detected in Ad5 infected cells and there was no significant difference in mRNA copies between the hFKs and the hFKs-E6 cells. However, in KH-900-infected cells, a few copies of E1A mRNA were detected in hGKs cells while 20 times more copies of E1A mRNA were detected in hFKs-E6 cells. More interestingly, more than 100 times of E1A mRNA were detected in KH-901 infected hFKs-E6 cells than in hFKs cells. In the meanwhile, the number of E1A mRNA copies was even lower in KH-901 infected hFKs cells than that in KH-900 infected hFKs cells. Taken together, it is demonstrated that theMtelo promoter, when being linked with report gene, has a higher level of activity and tumor cell-selectivity than that of telo promoter; at the same time, the improved tumor selectivity is true when the promoter is inserted into the adenoviral genome. The Mtelo promoter has better tumor specificity than the wild-type promoter when it is used to control the essential viral genes.

This result was firmed additionally in the cultured human bone marrow cells. In a cell viability assay, KH-900 and KH-901 were used to infect 293 cells and human bone marrow mesenchymal stem cells (hBMsc) at MOI of 1. Result presented in FIG. 8 showed that KH-901 killed 293 cells as efficiently as KH-900, however, KH-900 had a certain level of cell killing in hBMsc cells, while KH901 had no killing at all.

EXPERIMENT 2

Comparison of Tumor Cell Killing Capability of Four Conditionally Replicating Oncolytic Adenoviruses Recombinant Lung cancer cell line A549 was used to compare the killing capability of four conditionally replicating oncolytic adenoviruses. Cells were seeded in 6-cem dishes and viruses were applied at a MOI of 1 when cells grew to 85% in confluence. Cell viability was determined at various time points following infection (Hallenbeck et al. (1997) *Human Gene Therapy* 11:1172-1179). Result presented in FIG. 9 showed that KH-904 killed cells more efficiently than KH-901 and KH-902, while KH-900 was the weakest one.

This result indicated that the improved hTERT promoter has stronger activity than the wild-type hTERT promoter. It also indicated that replacement of the knob in the fiber gene from serotype 35 may have better infectivity than the serotype 5. This conclusion was confirmed in a panel of cancer cells and normal human cells (Table 1). A panel of human tumor and normal cells was infected with different adenovirus variants for 72 hours and cell viability was measured as described above. The EC50 was calculated for the amount of virus required to kill 50% of cells. The smaller the EC50, the better efficient a virus kills the cells. The result presented in Table 1 indicated that (1) KH-901 killed tumor cells more efficiently than KH-900, further confirming that the improved hTERT promoter has better tumor specificity; (2) KH-902 and KH-903 killed cells similarly to KH-901 while KH-904 was the strongest. In contrast, the improved Mtelo promoter containing viruses (KH-901, KH-902, KH-903 and KH-904) killed less normal cells compared to KH-900, the virus has the wild-type hTERT promoter. For KH-906, in which the viral E1B gene was linked to E1A by the IRES, had a good tumor cell-specificity even though the killing capability was relatively lower.

TABLE 1

GM-CSF expression in KH-901-infected cells

| Cell | KH-901 infected unit/cell | ELISA (ng/10^6 cells/24 hrs) | Bioassay (ng/10^6 cells/24 hrs) |
|---|---|---|---|
| LNCaP | 10 | 231 ± 21 | 195 ± 34 |
| LNCaP | 1 | 30 ± 9 | 15 ± 4 |
| Hep3B | 10 | 422 ± 13 | 355 ± 44 |
| Hep3B | 1 | 94 ± 6 | 85 ± 12 |
| SW680 | 10 | 527 ± 19 | 325 ± 44 |
| SW680 | 1 | 214 ± 4 | 135 ± 21 |
| A549 | 10 | 748 ± 17 | 625 ± 94 |
| A549 | 1 | 83 ± 2 | 55 ± 24 |
| HeLa | 10 | 120 ± 11 | 105 ± 56 |
| HeLa | 1 | 9 ± 1 | 2 ± 0.3 |
| hFKs | 10 | 5 ± 0.25 | 3.5 ± 0.4 |
| hFKs | 1 | undetectable | undetectable |

TABLE 2

EC50 of KH-900, KH-901, KH-902, KH-903, KH-904, and KH906

| cell | KH-900 | KH-901 | KH-902 | KH-903 | KH-904 | KH-906 |
|---|---|---|---|---|---|---|
| LoVo | 1.25 | 0.92 | 0.85 | 0.97 | 0.35 | 1.01 |
| A549 | 0.58 | 0.19 | 0.28 | 0.49 | 0.08 | 0.39 |
| LNCaP | 2.31 | 0.22 | 0.36 | 0.15 | 0.01 | 1.75 |
| Hep3B | 4.03 | 0.31 | 0.53 | 0.71 | 0.03 | 1.71 |
| HeLa | 3.85 | 0.62 | 0.55 | 0.73 | 0.25 | 0.89 |
| SW620 | 2.04 | 0.20 | 0.34 | 0.23 | 0.04 | 2.53 |
| CA-33 | 3.40 | 1.15 | 1.17 | 0.75 | 0.20 | 3.15 |
| HepG2 | 0.91 | 0.37 | 0.41 | 0.97 | 0.21 | 1.17 |
| SCC4 | 9.21 | 2.10 | 3.28 | 2.30 | 0.61 | 8.10 |
| HUVEC | 27.9 | 99.3 | 130.4 | 83.5 | 70.6 | 268.3 |
| BJ | 60.8 | 295.4 | 260.5 | 75.4 | 1801.8 | 435.4 |
| RPE | 35.4 | 231.7 | 295 | 431.7 | 295.3 | 531.7 |
| WI38 | 46.5 | 92.33 | 79.5 | 82.33 | 69.2 | 192.33 |
| MRC5 | 51.54 | 121.20 | 135.84 | 91.20 | 61.74 | 266.23 |

What's more interesting is that, to human normal cell, the viral recombinants that have been engineered to include. the genetically improved Mtelo promoter, including HK-901, HK-902, HK-903, HK-904, all show a much weaker killing capability (indicated by a higher EC50) than HK-900 that has been engineered to include the wild-type hTERT promoter.

In addition, the adenovirus recombinants KH-906, in which an internal ribosome entry site was inserted between the E1A and E1B genes, and therefore transcription of the E1A and E1B genes is under the control of the improved Mtelo promoter, has demonstrated a higher tumor cell-selectivity than the other viral recombinants, even though its killing capability towards tumor cells was a bit weaker than the other ones.

EXPERIMENT 3

KH-901 Produces a High Level of Biologically Active GM-CSF in Tumor Cells

Five tumor cell lines and one normal human cell line were infected with KH-901 at MOI of 1 or 10. 48 hours following the infection, cells were harvested for the determination of GM-CSF concentration by ELISA and the TF-1 assay as previously described (Li et al. (2001) *Cancer Research* 61:6428-6436). Result presented in FIG. 14 showed that 5 KH-901 infected tumor cells produced a high level of GM-CSF. For example, in KH-901 infected LNCaP cells, amount of GM-CSF detected in the cells was 231 ng/10^6 cells/24 hrs. In contrast, there was a very low level of GM-CSF detectable in KH-901 infected normal human cells. The bioassay further revealed that GM-CSF expressed in the tumor cells was biologically active (please see Table 2)

EXPERIMENT 4

Anti-tumor Efficacy of Oncolytic Adenovirus Recombinants in Tumor Models

Anti-tumor efficacy of oncolytic adenoviruses was assessed in prostate cancer LNCaP tumor model of nude mouse. Six millions of LNCaP cells were inoculated subcutaneously in nude mice and viruses were intratumorally injected for three times on day 1, 5 and 9 at a dose of $3\times10^{\wedge}10$ particles of various viruses (KH-901, KH-904 and addl1520, a E1B-p55 deleted oncolytic adenovirus) when the tumor volume reached 200 mm^3 within 4 weeks. Tumor volume was measured twice a week and the result was presented in FIG. 10.

In this test, three recombinants, that is to say, KH-901, KH-904 and KH-907 (not shown, the same as KH-901 but without GM-CSF gene), were used for tumor injection; Addl520 was also tested as control.

As can be seen from FIG. 10, tumor grew very fast for the placebo treatment, by 48 day the tumor volume had reached 1200% of the baseline. In the KH-901 treated group, the tumor remains the same as baseline, while the KH-904 treated tumors were reduced in volume to 15% of the baseline. During the same period of time, tumors treated with addl1520 had grown to 850% of the baseline.

This result indicated that KH-901 and KH-904 had a better anti-tumor activity than Addl1520 (Onyx-015). Interestingly, as demonstrated in the in vitro study, KH-904 had better anti-tumor efficacy than KH-901.

In the same study, GM-CSF expression was also documented. No GM-CSF was detected in KH-907 and Addl1520 treated animals while a high level of GM-CSF was detectable in KH-901 or KH-904 treated animals. For example, at day 14, amount of GM-CSF detected in the KH-901 or KH-904-treated animals was 2.322 g/mL or 2.776 g/mL, respectively. This result suggested that oncolytic virus KH-901 and likes produced GM-CSF not only in tumor cells but also a high expression in vivo in tumor-bearing animals.

The results of these studies show the replication of KH-901 and likes in a variety of tumor cells that high levels of GM-CSF expression are detected following infection.

The other oncolytic adenoviruses described above were also characterized by following similar procedure and will be described in more detail in the respective examples.

Recombinant replicating oncolytic adenoviruses described in this invention have the following features:

1. Structural Features

These recombinants are live viruses, and can replicate and propagate in tumor cells. They are different from synthesized and genetically engineered medicines. They are able to replicate in tumor cells, express foreign genes and have high biological activity as well as anti-tumor activity. These recombinants have immune-stimulating genes, therefore the immune-stimulating gene can be expressed in the virus infected cells and induce tumor cell-specific immune responses. They are safe because of the presence of tumor-specific regulatory element.

2. Potential Applications

The tumor-specific regulatory elements in the recombinant viruses are active in over 90% tumor cells, that is, in the majority of tumor cells, the critical gene of these recombinant viruses are under the control of tumor-specific promoter, therefore, these recombinant viruses can replicate in the majority of tumor cells and kill them. Thus these recombinant viruses have various potential applications, including for treatment of head and neck cancer, lung cancer, colon cancer, prostate cancer, bladder cancer, stomach cancer, and liver cancer, etc.

Because these recombinant viruses have the immune-stimulating gene as described above, the viruses will not only have oncolytic effects by killing tumor cells, but also will stimulate tumor-pecific immune responses following the expression of the cytokine in tumor cells. Thus, these viruses will not only be effective to local tumor but also be efficacious to distant tumor cells.

The recombinant viruses according to the invention have the following features: 1) they are more specific to tumor cells, while not infectious to normal somatic cells, stem cells; therefore these viruses may have less side-effect in clinical application; 2) they express immune-stimualting gene, including the secreted and membrane bound forms. This cytokine will stimulate tumor specific immune responses, thus they may be also effective to distant tumors; 3) through the modification to the viral capsid, these adeoviruses have better cell infectivity, thus they may have better anti-tumor activity.

This invention has the following contribution:

1) Through modification by targeted mutagenesis, the tumor specific regulatory element hTERT promoter has higher transcription activity and tumor specificity, the resulted promoter has a better targeting capability, has significantly reduced the transcription activity of the linked gene in normal somatic cells, especially in the sex cells, the progenitors and stem cells. The oncolytic adenoviruses, whose critical gene is under the control of the improved hTERT promoter, can not replicate in the bone marrow cells, but is highly potent in many tumor cells.

2) The immune-stimulating GM-CSF has been engineered in the recombinant adenoviruses so that GM-CSF will be expressed only in the virus infected cells. Such a virus can kill tumor cells via oncolytic effects following intratumoral injection, in the meanwhile, following the oncolytic lysis, virus infected cells express GM-CSF, which stimulates strong immune responses against tumor cells. Particularly, GM-CSF expressing oncolytic adenovirus will also have prevention effect because the virus will educate patient's immune system through the combination of oncolytic effect (cell killing and antigen presentation) and immune response through educating patient's immune cells. Therefore, such a virus may be able to prevent patient from recurrence of tumors.

3) Through the modification of capsid, the resulted recombinant oncolytic adenovirus has better tumor infectivity. Due to non- or low expression of adenovirus receptor CAR of the adenovirus serotype 5, it's quite often that the Ad5 could not infect tumor cell well. However, when the Ad5 genome is incorporated with the binding site and the sequence for the receptor of Adenovrius serotype 35, the infectivity to majority of the tumor cells can be greatly increased. In vitro and in vivo studies have confirmed this observation.

Description of the Sequences in the Sequence Listing

SEQ ID NO. 1 is a bp fragment containing sequences from the human TERT promoter, which has several transcription factor binding sites including SP-1 (GC-boxes), E-Boxes (the binding site for Myc), NF-1 (the site for binding NF factor).

SEQ ID NO. 2 is a human TERT promoter improved by mutagenesis, which has a higher tumor cell-selectivity and transcription activity; E2F-1: binding site of the transcription factor E2F.

SEQ ID NO. 3 is a sequence from the full length of KH-901, in which
1) 1-103: adenoviral left ITR {sequence of adenovirus serotype 5, shown in Genbank NO. BK000408};
2) 194-358: adenovirus packaging sequence and the enhancing sequence for E1;
3) 362-534: SV40 poly(A) signal sequence and linker (the sequence of adenovirus serotype 5 from which np 362 to 551 have been deleted);
4) 525-811: the sequences of the improved hTERT promoter and the linker;
5) 812 to the right: adenovirus sequence including E1A, E1B, E2, etc.;
6) 28995-29436: human immune-stimulating GM-CSF gene;
7) 29437 to the right: adenovirus sequence including E4 gene and the right end;

SEQ ID NO. 4 is an immune regulatory element GM-CSF in membrane-bound form (mbGM-CSF), contained in the genome of the recombinant.

SEQ ID NO. 5 is a from chimeric fiber protein sequence in the genome of recombinant KH-904, in which the fiber knob of the fiber gene is from serotype 35 of human adenovirus.

BRIEF DESCRIPTION OF THE DRAWINGS

FIG. 1 depicts the sequence of the human telomerase reverse transcriptase promoter and binding sites for transcription factors. SP-1 (GC-boxes): SP 1 binding sites, E-Boxes: Myc binding site, NF-1: NF binding site.

FIG. 3-1 and FIG. 3-2: depicts the structures of the recombinants according to the invention.

FIG. 4-1, FIG. 4-2 and FIG. 4-3: depicts the process of generating recombinant adenovirus variant KH-901.

SPECIFIC EMBODIMENTS

The following examples were given and served to further describe the details of the invention, which shall not represent any limitation to this invention.

EXAMPLE 1

Figures 1, 4:
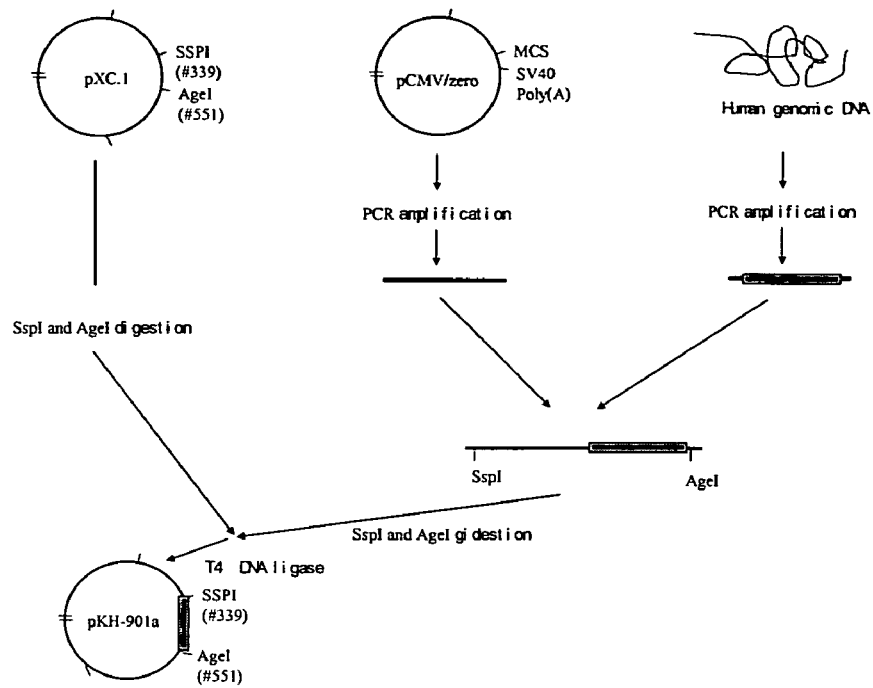
Figures 2, 4:
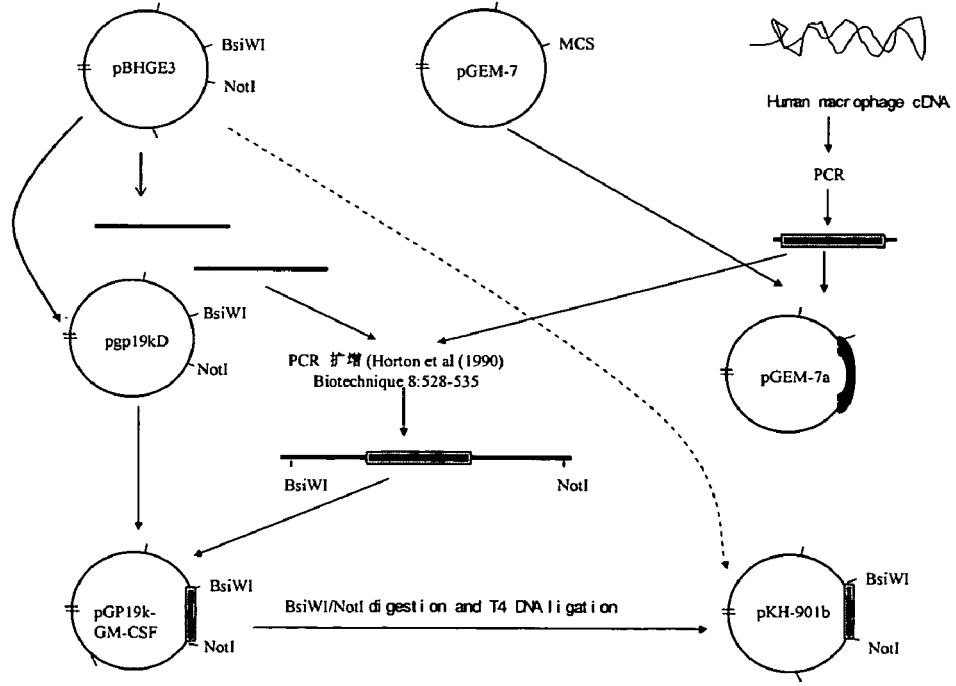
Figures 3, 4:
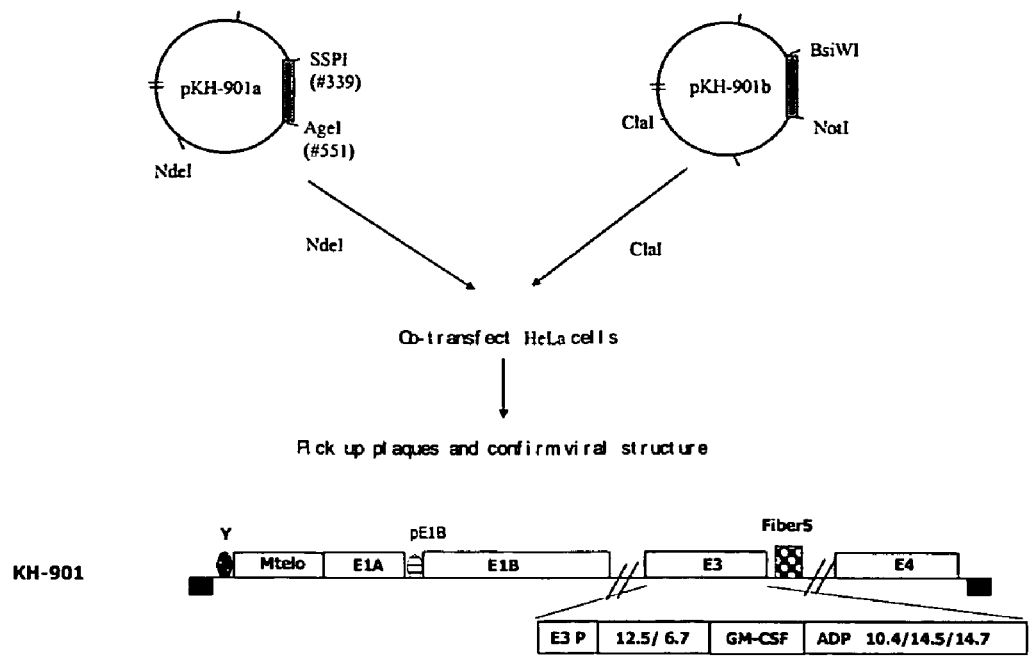
Figure 5:
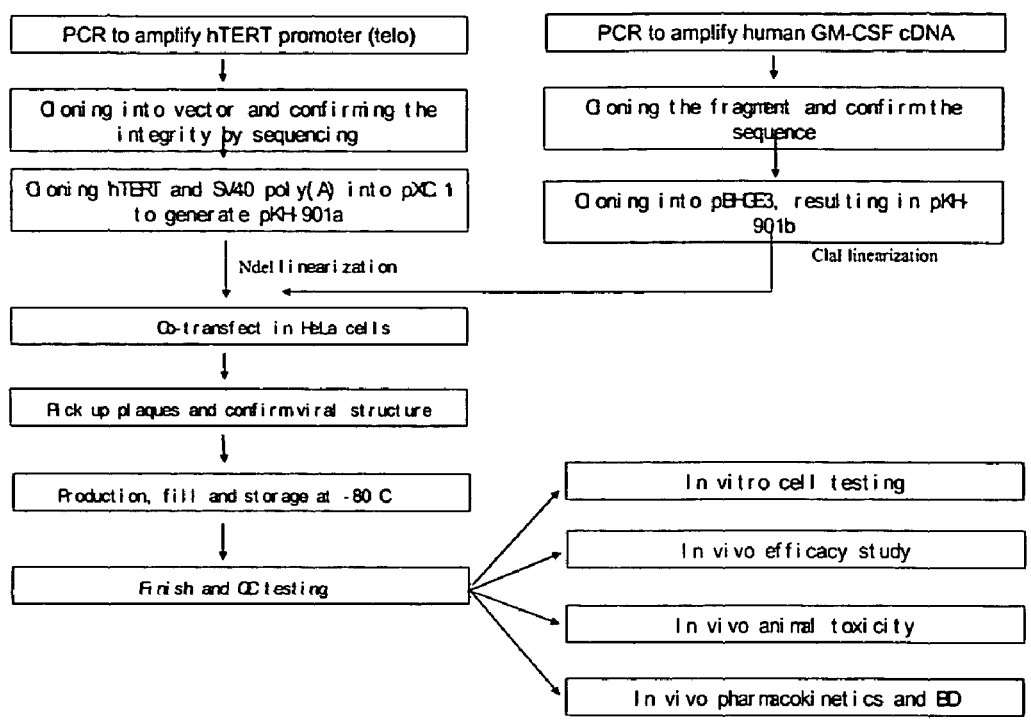
FIG. 5 shows the details of construction of recombinant KH-901
Figure 6:
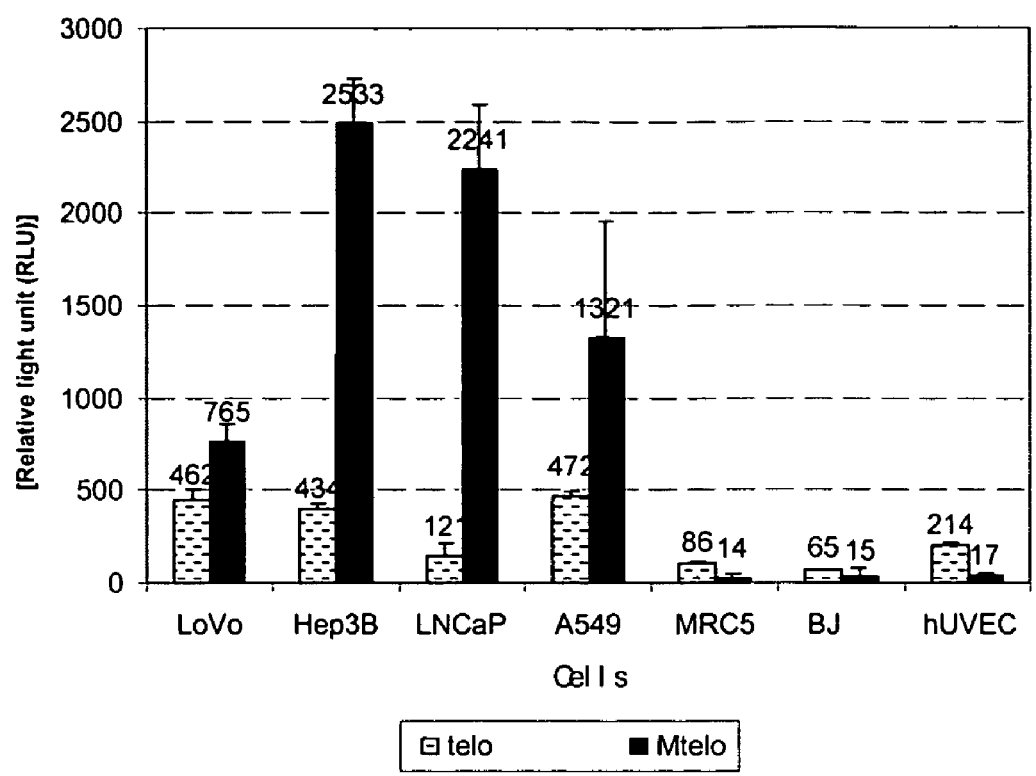
FIG. 6 shows the promoter activity for both the wild-type hTERT (telo) and the improved mhTERT promoters (Mtelo).
Figure 7:
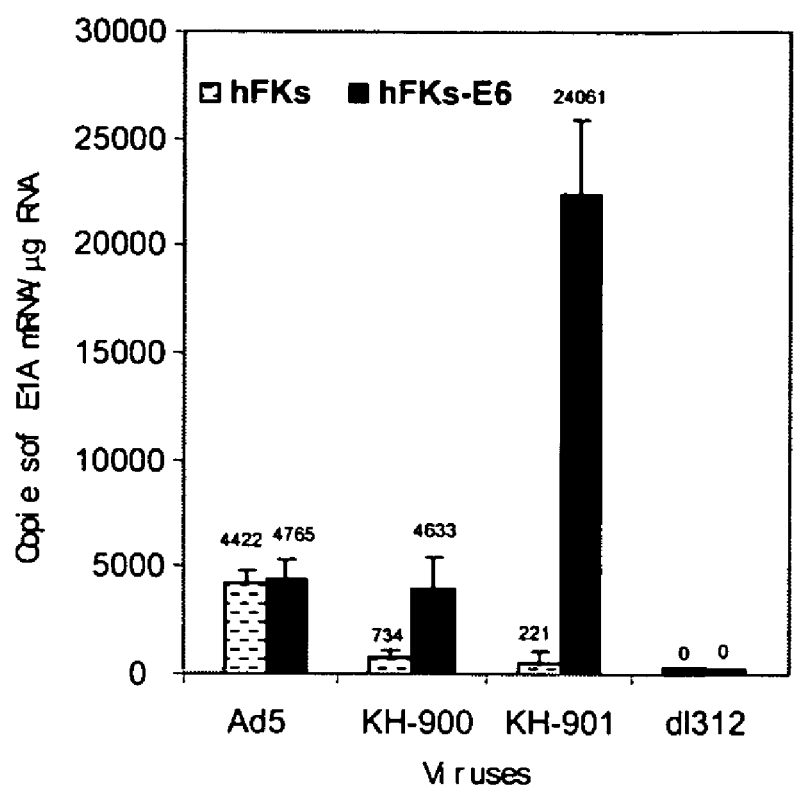
FIG. 7 shows the E1A message RNA expression of the recombinant adenovirus in hFK cells and hFKs-E6, which is capable of transforming HPV E6 gene.
Figure 8:
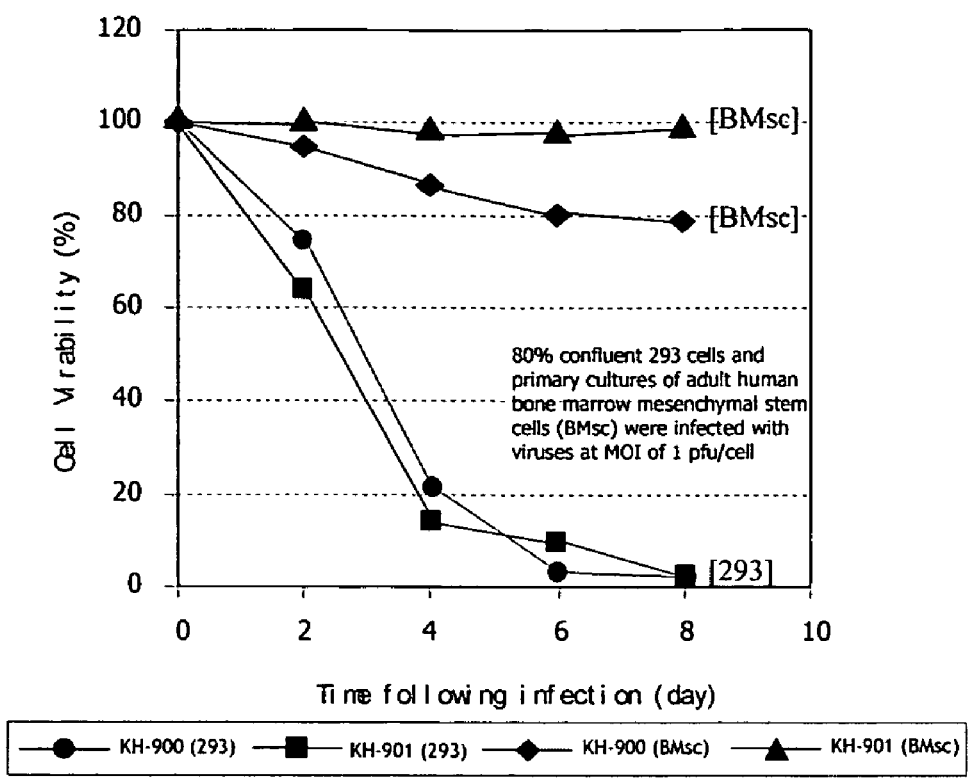
FIG. 8 shows cytolytic activity of recombinant adenoviruses to normal human bone marrow mesenchymal stem cells.
Figure 9:
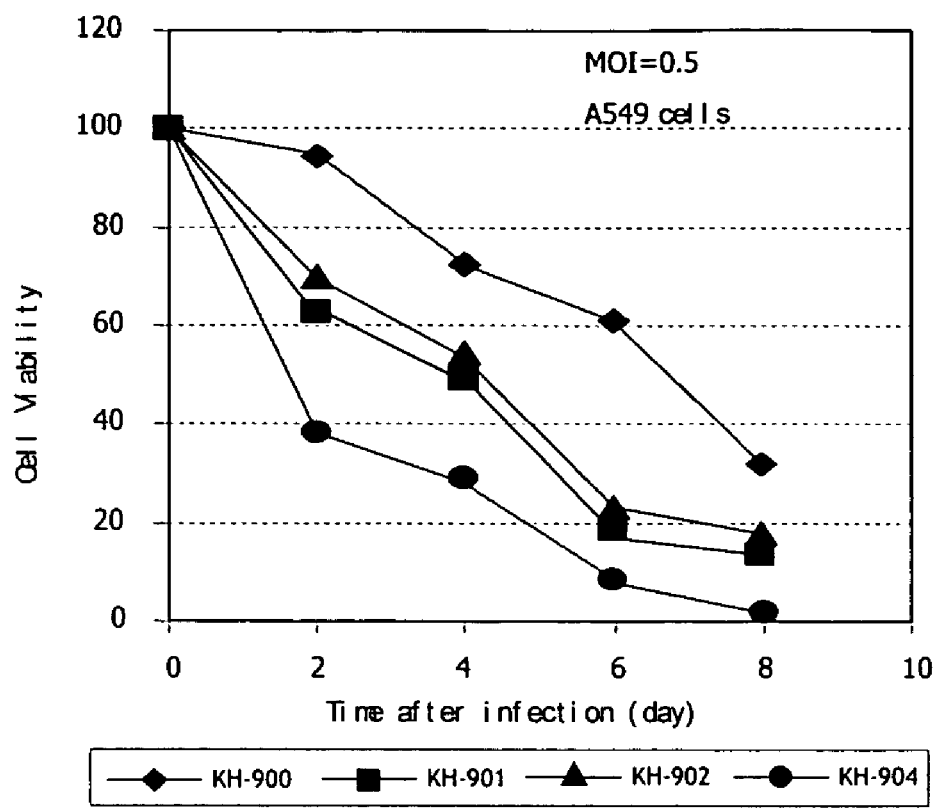
FIG. 9 shows cytolytic activity of recombinant adenoviruses in A549 cells (cell viability %).
Figure 10:
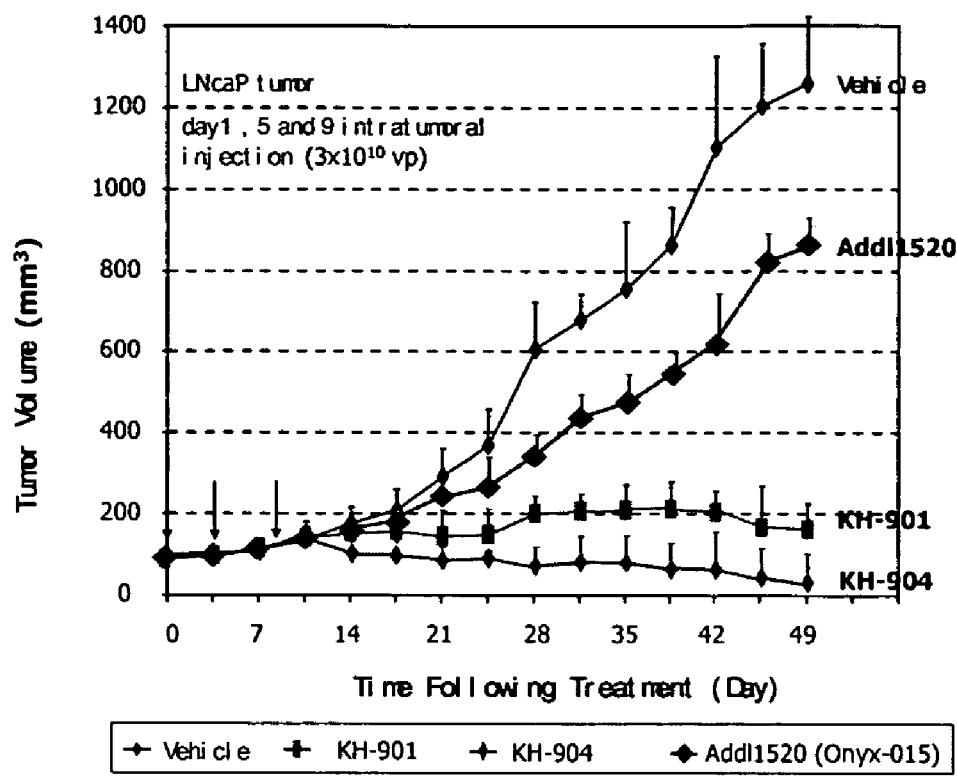
FIG. 10 shows anti-tumor efficacy in prostate cancer LNCaP xenografts model following intratumor injection of recombinant adenoviruses.

1. Construction of replicating oncolytic adenovirus recombinant KH-901 and its analysis (FIG. 4 and FIG. 5).
2. According to the sequence of the hTERT promoter shown in FIG. 1, two primers as follow were synthesized:

A. 5'-GTC TGG ATC CGC TAG CCC CAC G-3'

B. 5'-CGA CCG GTG ATA TCG TTT AAT TCG C-3'

Figure 2:
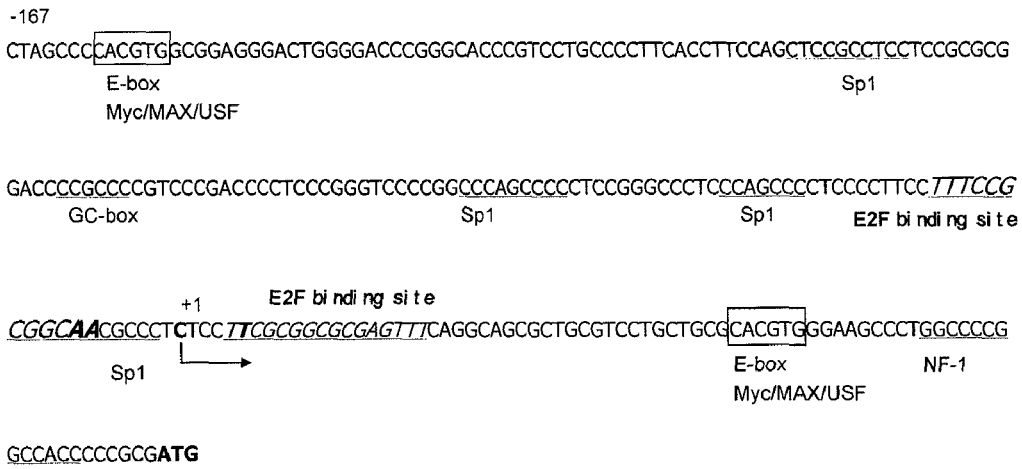
FIG. 2 depicts the human TERT promoter improved by a mutagenesis, which has a higher tumor cell-selectivity and reverse transcription activity; E2F-1: binding site of the transcription factor E2F.
Figures 1, 3:
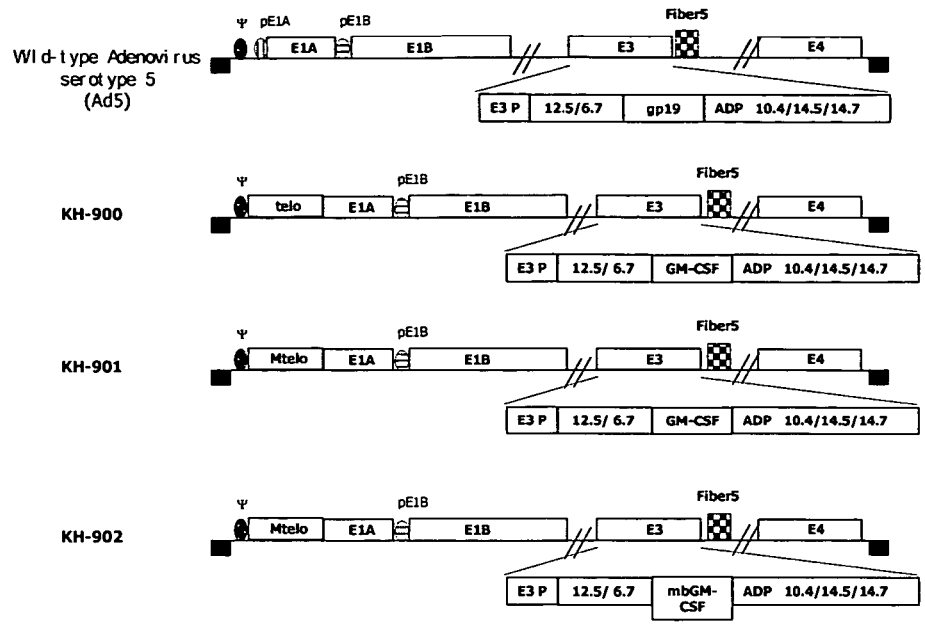
Figures 2, 3:
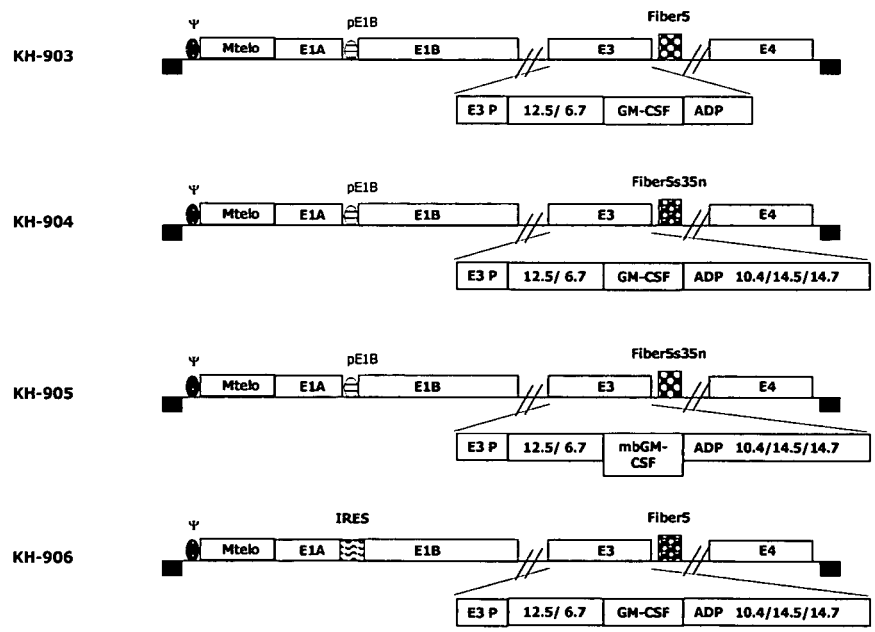

For the amplification of the hTERT promoter by PCR method, in which the activated human RNA was used as template. Conditions for the PCR reaction was as follows: for the first cycle, 94° C. denature for 5 minutes, 81° C. annealing for 1 minute and 72° C. for extension for 2 minutes. For each of the succeeding cycle, 93° C. denature for 1 minute, then subject to agar gel analysis and hTERT promoter fragment was recovered. It was indicated by sequencing that the obtained promoter fragment is the same as that as the disclosed (FIG. 1). This fragment of DNA was then cloned onto pUC19 vector, and reformed it to the sequence as shown in FIG. 2 by mutagenesis via a kit from Strategene (Strategene, Calif.).

3. The poly(A) signal sequence was amplified by PCR with the following primers:

C. 5'-TAATATTTGTCTAGGGCCGCGGGGGATCTCTGC-3'

D. 5'-GGATCCAGACATGATAAGATACATTGAGAG-3'

Wherein Pcmv/ZERO (Invitrogen, USA) was used as the template, the condition for annealing during the PCR reaction was the same as above. The PCR fragment was purified and confirmed by sequencing.

4. The purified hTERT promoter fragment and the poly(A) DNA fragment were denatured together at 95° C. for 5 minutes and cooled down to room temperature as the template. A DNA fragment having about 500 basepairs was amplified with primers A and D, the purifed and sequenced PCR fragment was digested with SspI and AgeI, and further purifed fragment containing poly (A) signal sequence and the hTERT promoter was used for the subsequent cloning process.

5. pXC.1 (purchased from Microbix, Canada) was used as the template and two enzyme sites were added at nucleotide 339 (SspI) and 551 (PinAI) via mutagenesis. The mutated pXC.1 was digested with SspI and PinAI and purified, with the large fragemtn as the vector. The Poly(A)/hTERT fragemtn as inserted was ligated with the pXC.1 vector, and transformed into *E. Coli* DH5 by common cloning techniques following 20 hours. After an incubation at 4° C. for 30 minutes, thermal shocking at 42° C. for 30 seconds, and further incubation 4° C. for 2 minutes, then culturing it at 37° C. for 45 minutes with 1 mL LB culturing solution. Then it was moved to an agar culturing plate containing ampcilin for 24 hour's culture; individual bacteria were picked up using sterilized toothstick and moved to clean culturing bottle that contains 1 ml LB for 24 hours. The plasmid DNA was purified from cultured *E. coli* and confirmed the structure by enzyme digestion, named it as pKH-901a. This plasmid contains the left ITR, the packaging signal, the poly(A) sequence, the hTERT promoter (Mtelo), E1A, and partial E1B, 6. Construction of the right end of the adenovirus pGEM-7 vector (available from Promega company). Then the two pairs of primers were used to amplify two DNA fragments:

E. 5'-AACCAAGGCGAACCTT-3'

F. 5'-CCACATGGTTATCTTGG-3'

-continued

G. 5'-CCAGTCCAGGAGTAATTTAC-3'

H. 5'-TGCGCTTTAGGCAGCAGATG-3'

To clone GM-CSF gene, the following primers were used:

M. 5'-CCACCCAAGATAACCATGTGGCTGC-3'

N. 5'-AACTTAGTAAATTACTCCTGGACTGG-3'.

A large amount of cDNA fragment of the GM-CSF was amplified from cDNA template prepared from the activated macrophages by PCR with a sirmilar amplification condition described above. Sequence of the cDNA was confirmed by sequencing following purification, the cDNA fragment was mixed with two DNA fragment amplified from pBHGE3 as template for further amplification by PCR with primers E and H to produce a large DNA fragment. Sequence of this resulting DNA fragment was confirmed by sequencing, and the DNA fragment was cloned into pGEM-7 vector following digestion with BsiWI and NotI, subsequently ligated into pBHGE3, resulted in a plasmid pKH-901b. This left end plasmid contains most portion of the E1B gene, the entire E2 gene, the entire E3 genes, the GM-CSF gene and the E4 gene.

7. Construction of recombinant adenovirus KH-901 pKH-901a and pKH-901b plasmid DNAs were lineraized with restriction endonuclease NdeI and ClaI and co-transfected into HeLa cells (with transfectin from Invitrogen) following purification of the plasmid DNA. Cells were harvested after incubation at 37 C for 10 days. 100 uL of supernatant was taken for plaque assay following 3 cycles of freeze/thaw. Single plaques were seen under low-melting agar 8 to 12 days after adding the supernatant. 10 uL of liquid under the agar was picked up by 10-uL auto-pipeteman and added to the pre-seeded HeLa cells. Cell lysate was seen and collected 4 to 8 days after inoculation. 200 uL of cell lysate was used for DNA extraction. Viral structure was confirmed by PCR and Southern blot. Individual plaques were further purified in HeLa cells and grown in HeLa cells for virus stock. Virus stock was stored at −80 C freezer. An aliquot of virus stock was taken for sequencing confirmation and the virus was named as KH-901.

The method for large scaled production of KH-901 will be described separately, however, it is briefed here, HeLA-S3 cells (HeLa cells were adapted to be able to grow in serum-free medium) were cultured at 3 liter bioreactor, when cell number reaches 3 million per liter, cells were infected with KH-901, and continued to culture for 2-3 days. Cells then were harvested and virus was purified through CsC12 gradient purification or ion exchange column. The purified was stored in proper buffer such as PBS and glycerol.

EXAMPLE 2

KH-900 was constructed following a similar routine to that for KH-901, except that no poly (A) was contained in the plasmid pKH-901a and no mutantan in the hTERT promoter fragment; the sequence is the same to SEQ. ID No. 1. The resulted plasmid isnamed as pKH-900a; pKH-900a were co-transfected with pKH-901b in HeLa cells to generate KH-900.

EXAMPLE 3

For KH-902 construction, the cDNA of GM-CSF in pKH-901b was replaced with the membrane bound version as shown by SEQ ID NO. 4, resulting in pKH-902b. pKH-901a and pKH-902b were co-transfected in HeLa cells to generate KH-902.

EXAMPLE 4

For making KH-903, the encoding regions for 10.4 k, 14.5 k and 14.7 k in pKH-901b were deleted by conventional genetically-engineering method, resulting in a plasmid called KH-903b. pKH-901a and pKH-903b were co-transfected in HeLa cells to generate KH-903.

EXAMPLE 5

For making KH904, the knob of the fiber gene, i.e., the adenovirus serotype 5 was replaced with the knob from adenovirus serotype 35, as shown in SEQ ID NO. 5, resulting in a plasmid called pKH-904b.

EXAMPLE 6

For making KH-905, the cDNA of the GM-CSF gene in pKH-904b was replaced with the membrane bound version, as shown in SEQ ID NO. 4, resulting in a plasmid called pKH-905b. pKH-901a and pKH-905b were co-transfected in HeLa cells to generate KH905. Viral structure was confirmed by PCR and sequencing.

EXAMPLE 7

For generating KH-906, the endogenous promoter for E1B was replaced with the internal ribosome entry signal, resulting in a plasmid called pKH-906a. pKH-906a and pKH-901b were co-transfected in HeLa cells to generate KH-906 (Li et al. (2001) Cancer Research 62:2667-2674). Viral structure was confirmed by PCR and sequencing.

SEQUENCE LISTING

<160> NUMBER OF SEQ ID NOS: 5

<210> SEQ ID NO 1
<211> LENGTH: 252
<212> TYPE: DNA
<213> ORGANISM: Homo sapiens

<400> SEQUENCE: 1
ctagccccac gtggcggagg gactggggac ccgggcaccc gtcctgcccc ttcaccttcc     60

```
agctccgcct cctccgcgcg daccccgccc cgtcccgacc cctcccgggt ccccggccca    120 gcccctccg  ggccctccca  gcccctcccc  ttcctttccg  cggccccgcc  ctctcctcgc    180
ggcgcgagtt tcaggcagcg ctgcgtcctg ctgcgcacgt gggaagccct ggccccggcc    240 accccccgcga tg                                                       252
```

```
<210> SEQ ID NO 2
<211> LENGTH: 253
<212> TYPE: DNA
<213> ORGANISM: Artificial Sequence
<220> FEATURE:
<223> OTHER INFORMATION: human TERT promoter improved by mutagenesis

<400> SEQUENCE: 2
ctagccccac gtggcggagg gactggggac ccgggcaccc gtcctgcccc ttcaccttcc     60
agctccgcct cctccgcgcg gaccccgccc cgtcccgacc cctcccgggt ccccggccca    120 gcccctccg  ggccctccca  gcccctcccc  ttcctttccg  cggcaacgcc  ctctccttcg    180
cggcgcgagt tcaggcagc  gctgcgtcct gctgcgcacg tgggaagccc tggccccggc    240
cacccccgcg atg                                                       253
```

```
<210> SEQ ID NO 3
<211> LENGTH: 36152
<212> TYPE: DNA
<213> ORGANISM: Artificial Sequence
<220> FEATURE:
<223> OTHER INFORMATION: Recombinant sequence from the full length of
      KH-901

<400> SEQUENCE: 3
catcatcaat aatataccttt attttggatt gaagccaata tgataatgag ggggtggagt     60
ttgtgacgtg gcgcggggcg tgggaacggg gcgggtgacg tagtagtgtg gcggaagtgt    120
gatgttgcaa gtgtggcgga acacatgtaa gcgacggatg tggcaaaagt gacgtttttg    180
gtgtgcgccg gtgtacacag gaagtgacaa ttttcgcgcg gttttaggcg gatgttgtag    240
taaatttggg cgtaaccgag taagatttgg ccattttcgc aggaaaactg aataagagga    300
agtgaaatct gaataatttt gtgttactca tagcgcgtaa tatttgtcta gggccgcggg    360
ggatctctgc aggaatttga tatcaagctt atcgataccg tcgaaacttg tttattgcag    420
cttataatgg ttacaaataa agcaatagca tcacaaattt cacaaataaa gcatttttt    480 cactgcattc tagttgtggt ttgtccaaac tcatcaatgt atcttatcat gtctggatcc    540
gctagcccca cgtggcggag ggactgggga cccgggcacc cgtcctgccc cttcaccttc    600
cagctccgcc tcctccgcgc ggaccccgcc ccgtcccgac ccctcccggg tccccggccc    660
agccccctcc gggccctccc agcccctccc cttcctttcc gcggcaacgc cctctccttc    720
gcggcgcgag tttcaggcag cgctgcgtcc tgctgcgcac gtgggaagcc ctggccccgg    780
ccacccccgc gaattaaacg atatcaccgg tcgactgaaa atgagacata ttatctgcca    840
cggaggtgtt attaccgaag aaatggccgc cagtctttttg gaccagctga tcgaagaggt    900
actggctgat aatcttccac ctcctagcca ttttgaacca cctacccttc acgaactgta    960
tgatttagac gtgacggccc ccgaagatca caacgaggag gcggtttcgc agatttttcc    1020
cgactctgta atgttggcgg tgcaggaagg gattgactta ctcactttc cgccggcgcc    1080 cggttctccg gagccgcctc acctttcccg gcagccgag cagccggagc agagagcctt    1140
gggtccggtt tctatgccaa accttgtacc ggaggtgatc gatcttacct gccacgaggc    1200
tggctttcca cccagtgacg acgaggatga agagggtgag gagtttgtgt tagattatgt    1260
```

```
ggagcacccc gggcacggtt gcaggtcttg tcattatcac cggaggaata cgggggaccc   1320
agatattatg tgttcgcttt gctatatgag gacctgtggc atgtttgtct acagtaagtg   1380
aaaattatgg gcagtgggtg atagagtggt gggtttggtg tggtaatttt tttttttaatt  1440 tttacagttt tgtggtttaa agaattttgt attgtgattt ttttaaaagg tcctgtgtct   1500
gaacctgagc ctgagcccga gccagaaccg gagcctgcaa gacctacccg ccgtcctaaa   1560
atggcgcctg ctatcctgag acgcccgaca tcacctgtgt ctagagaatg caatagtagt   1620
acggatagct gtgactccgg tccttctaac acacctcctg agatacaccc ggtggtcccg   1680
ctgtgcccca ttaaaccagt tgccgtgaga gttggtgggc gtcgccaggc tgtggaatgt   1740
atcgaggact tgcttaacga gcctgggcaa cctttggact tgagctgtaa acgcccagg   1800 ccataaggtg taaacctgtg attgcgtgtg tggttaacgc ctttgtttgc tgaatgagtt   1860
gatgtaagtt taataaaggg tgagataatg tttaacttgc atggcgtgtt aaatggggcg   1920
gggcttaaag ggtatataat gcgccgtggg ctaatcttgg ttacatctga cctcatggag   1980
gcttgggagt gttttggaaga tttttctgct gtgcgtaact tgctggaaca gagctctaac   2040
agtacctctt ggttttggag gtttctgtgg ggctcatccc aggcaaagtt agtctgcaga   2100
attaaggagg attacaagtg ggaatttgaa gagcttttga aatcctgtgg tgagctgttt   2160
gattctttga atctgggtca ccaggcgctt ttccaagaga aggtcatcaa gactttggat   2220
ttttccacac cggggcgcgc tgcggctgct gttgcttttt tgagttttat aaaggataaa   2280
tggagcgaag aaacccatct gagcgggggg tacctgctgg attttctggc catgcatctg   2340
tggagagcgg ttgtgagaca caagaatcgc ctgctactgt tgtcttccgt ccgcccggcg   2400
ataataccga cggaggagca gcagcagcag caggaggaag ccaggcggcg gcggcaggag   2460
cagagcccag gaacccgaga gccggcctgg accctcggga atgaatgttg tacaggtggc   2520
tgaactgtat ccagaactga gacgcatttt gacaattaca gaggatgggc aggggctaaa   2580
gggggtaaag agggagcggg gggcttgtga ggctacagag gaggctagga atctagcttt   2640
tagcttaatg accagacacc gtcctgagtg tattactttt caacagatca aggataattg   2700
cgctaatgag cttgatctgc tggcgcagaa gtattccata gagcagctga ccacttactg   2760
gctgcagcca ggggatgatt ttgaggaggc tattagggta tatgcaaagg tggcacttag   2820
gccagattgc aagtacaaga tcagcaaact tgtaaatatc aggaattgtt gctacatttc   2880
tgggaacggg gccgaggtgg agatagatac ggaggatagg gtggcctttga gatgtagcat   2940 gataaatatg tggccggggt gcttggcatg gacggggtgg ttattatgaa tgtaaggttt   3000
actggcccca attttagcgg tacggttttc ctggccaata ccaaccttat cctacacggt   3060
gtaagcttct atgggtttaa caatacctgt gtggaagcct ggaccgatgt aagggttcgg   3120
ggctgtgcct tttactgctg ctggaagggg gtggtgtgtc gccccaaaag cagggcttca   3180
attaagaaat gcctctttga aaggtgtacc ttgggtatcc tgtctgaggg taactccagg   3240
gtgcgccaca atgtggcctc cgactgtggt tgcttcatgc tagtgaaaag cgtggctgtg   3300
attaagcata acatggtatg tggcaactgc gaggacaggg cctctcagat gctgacctgc   3360
tcggacggca actgtcacct gctgaagacc attcacgtag ccagccactc tcgcaaggcc   3420
tggccagtgt ttgagcataa catactgacc cgctgttcct tgcatttggg taacaggagg   3480
ggggtgttcc taccttacca atgcaatttg agtcacacta agatattgct tgagcccgag   3540
agcatgtcca aggtgaacct gaacggggtg tttgacatga ccatgaagat ctggaaggtg   3600
ctgaggtacg atgagacccg caccaggtgc agaccctgcg agtgtggcgg taaacatatt   3660
```

```
aggaaccagc ctgtgatgct ggatgtgacc gaggagctga ggcccgatca cttggtgctg    3720
gcctgcaccc gcgctgagtt tggctctagc gatgaagata cagattgagg tactgaaatg    3780
tgtgggcgtg gcttaagggt gggaaagaat atataaggtg ggggtcttat gtagttttgt    3840
atctgttttg cagcagccgc cgccgccatg agcaccaact cgtttgatgg aagcattgtg    3900
agctcatatt tgacaacgcg catgccccca tgggccgggg tgcgtcagaa tgtgatgggc    3960
tccagcattg atggtcgccc cgtcctgccc gcaaactcta ctaccttgac ctacgagacc    4020
gtgtctggaa cgccgttgga gactgcagcc tccgccgccg cttcagccgc tgcagccacc    4080
gcccgcggga ttgtgactga ctttgctttc ctgagcccgc ttgcaagcag tgcagcttcc    4140
cgttcatccg cccgcgatga caagttgacg gctcttttgg cacaattgga ttctttgacc    4200
cgggaactta atgtcgtttc tcagcagctg ttggatctgc ccagcaggt ttctgccctg    4260 aaggcttcct cccctcccaa tgcggtttaa aacataaata aaaaaccaga ctctgtttgg    4320
atttggatca agcaagtgtc ttgctgtctt tatttagggg ttttgcgcgc gcggtaggcc    4380
cgggaccagc ggtctcggtc gttgagggtc ctgtgtattt tttccaggac gtggtaaagg    4440
tgactctgga tgttcagata catgggcata agcccgtctc tggggtggag gtagcaccac    4500
tgcagagctt catgctgcgg ggtggtgttg tagatgatcc agtcgtagca ggagcgctgg    4560
gcgtggtgcc taaaaatgtc tttcagtagc aagctgattg ccaggggcag gcccttggtg    4620
taagtgttta caaagcggtt aagctgggat gggtgcatac gtgggatat gagatgcatc     4680 ttggactgta ttttaggtt ggctatgttc ccagccatat ccctccgggg attcatgttg      4740
tgcagaacca ccagcacagt gtatccggtg cacttgggaa atttgtcatg tagcttagaa    4800
ggaaatgcgt ggaagaactt ggagacgccc ttgtgacctc caagattttc catgcattcg    4860
tccataatga tggcaatggg cccacgggcg gcggcctggg cgaagatatt tctgggatca    4920
ctaacgtcat agttgtgttc caggatgaga tcgtcatagg ccattttttac aaagcgcggg    4980 cggagggtgc cagactgcgg tataatggtt ccatccggcc caggggcgta gttaccctca    5040
cagatttgca tttcccacgc tttgagttca gatgggggga tcatgtctac ctgcggggcg    5100
atgaagaaaa cggtttccgg ggtaggggag atcagctggg aagaaagcag gttcctgagc    5160
agctgcgact accgcagcc ggtgggcccg taaatcacac ctattaccgg gtgcaactgg      5220
agttaagaga gctgcagctg ccgtcatccc tgagcagggg ggccacttcg ttaagcatgt    5280
ccctgactcg atgttttccc tgaccaaatc cgccagaagg cgctcgccgc ccagcgatag    5340
cagttcttgc aaggaagcaa agttttttcaa cggtttgaga ccgtccgccg taggcatgct    5400
tttgagcgtt tgaccaagca gttccaggcg gtcccacagc tcggtcacct gctctacggc    5460
atctcgatcc agcatatctc ctcgtttcgc gggttggggc ggctttcgct gtacggcagt    5520
agtcggtgct cgtccagacg ggccagggtc atgtctttcc acgggcgcag ggtcctcgtc    5580
agcgtagtct gggtcacggt gaagggtgc gctccgggct gcgcgctggc cagggtgcgc     5640
ttgaggctgg tcctgctggt gctgaagcgc tgccggtctt cgccctgcgc gtcggccagg    5700
tagcatttga ccatggtgtc atagtccagc ccctccgcgg cgtggcccett ggcgcgcagc    5760 ttgcccttgg aggaggcgcc gcacgagggg cagtgcagac ttttgagggc gtagagcttg    5820
ggcgcgagaa ataccgattc cggggagtag gcatccgcgc cgcaggcccc gcagacggtc    5880
tcgcattcca cgagccaggt gagctctggc cgttcgggt caaaaaccag gtttcccca      5940 tgcttttga tgcgtttctt acctctggtt tccatgagcc ggtgtccacg ctcggtgacg     6000
aaaaggctgt ccgtgtcccc gtatacagac ttgagaggcc tgtcctcgag cggtgttccg    6060
```

```
cggtcctcct cgtatagaaa ctcggaccac tctgagacaa aggctcgcgt ccaggccagc    6120
acgaaggagg ctaagtggga ggggtagcgg tcgttgtcca ctaggggggtc cactcgctcc    6180 agggtgtgaa gacacatgtc gccctcttcg gcatcaagga aggtgattgg tttgtaggtg    6240
taggccacgt gaccgggtgt tcctgaaggg gggctataaa aggggggtggg ggcgcgttcg    6300 tcctcactct cttccgcatc gctgtctgcg agggccagct gttggggtga gtactccctc    6360
tgaaaagcgg gcatgacttc tgcgctaaga ttgtcagttt ccaaaaacga ggaggatttg    6420
atattcacct ggcccgcggt gatgcctttg agggtggccg catccatctg gtcagaaaag    6480
acaatctttt tgttgtcaag cttggtggca aacgacccgt agagggcgtt ggacagcaac    6540
ttggcgatgg agcgcagggt ttggttttg tcgcgatcgg cgcgctcctt ggccgcgatg    6600
tttagctgca cgtattcgcg cgcaacgcac cgccattcgg gaaagacggt ggtgcgctcg    6660
cgggcaccag gtgcacgcgc caaccgcggt tgtgcagggt gacaaggtca acgctggtgg    6720
ctacctctcc gcgtaggcgc tcgttggtcc agcagaggcg gccgcccttg cgcgagcaga    6780
atggcggtag ggggtctagc tgcgtctcgt ccggggggtc tgcgtccacg gtaaagaccc    6840
cgggcagcag gcgcgcgtcg aagtagtcta tcttgcatcc ttgcaagtct agcgcctgct    6900
gccatgcgcg ggcggcaagc gcgcgctcgt atgggttgag tgggggaccc catggcatgg    6960
ggtgggtgag cgcggaggcg tacatgccgc aaatgtcgta aacgtagagg ggctctctga    7020
gtattccaag atatgtaggg tagcatcttc caccgcggat gctggcgcgc acgtaatcgt    7080
atagttcgtg cgagggagcg aggaggtcgg gaccgaggtt gctacgggcg ggctgctctg    7140
ctcggaagac tatctgcctg aagatggcat gtgagttgga tgatatggtt ggacgctgga    7200
agacgttgaa gctggcgtct gtgagaccta ccgcgtcacg cacgaaggag cgtaggagt    7260 cgcgcagctt gttgaccagc tcggcggtga cctgcacgtc tagggcgcag tagtccaggg    7320
tttccttgat gatgtcatac ttatcctgtc cctttttttt ccacagctcg cggttgagga    7380
caaactcttc gcggtctttc cagtactctt ggatcggaaa cccgtcggcc tccgaacggt    7440
aagagcctag catgtagaac tggttgacgg cctggtaggc gcagcatccc ttttctacgg    7500
gtagcgcgta tgcctgcgcg gccttccgga gcgaggtgtg ggtgagcgca aggtgtccc    7560 tgaccatgac tttgaggtac tggtatttga agtcagtgtc gtcgcatccg ccctgctccc    7620
agagcaaaaa gtccgtgcgc ttttggaac gcggatttgg cagggcgaag gtgacatcgt    7680
tgaagagtat ctttcccgcg cgaggcataa agttgcgtgt gatgcggaag ggtcccggca    7740
cctcggaacg gttgttaatt acctgggcgg cgagcacgat ctcgtcaaag ccgttgatgt    7800
tgtggcccac aatgtaaagt tccaagaagc gcgggatgcc cttgatgaa ggcaatttt    7860 taagttcctc gtaggtgagc tcttcagggg agctgagccc gtgctctgaa agggcccagt    7920
ctgcaagatg agggttggaa gcgacgaatg agctccacag gtcacgggcc attagcattt    7980
gcaggtggtc gcgaaaggtc ctaaactggc gacctatggc catttttct ggggtgatgc    8040 agtagaaggt aagcgggtct tgttcccagc ggtcccatcc aaggttcgcg gctaggtctc    8100
gcgcggcagt cactagaggc tcatctccgc cgaacttcat gaccagcatg aagggcacga    8160
gctgcttccc aaaggcccccc atccaagtat aggtctctac atcgtaggtg acaaagagac    8220
gctcggtgcg aggatgcgag ccgatcggga agaactggat ctcccgccac caattggagg    8280
agtggctatt gatgtggtga aagtagaagt ccctgcgacg ggccgaacac tcgtgctggc    8340
ttttgtaaaa acgtgcgcag tactggcagc ggtgcacggg ctgtacatcc tgcacgaggt    8400
tgacctgacg accgcgcaca aggaagcaga gtgggaattt gagcccctcg cctggcgggt    8460
```

```
ttggctggtg gtcttctact tcggctgctt gtccttgacc gtctggctgc tcgaggggag   8520
ttacggtgga tcggaccacc acgccgcgcg agcccaaagt ccagatgtcc gcgcgcggcg   8580
gtcggagctt gatgacaaca tcgcgcagat gggagctgtc catggtctgg agctcccgcg   8640
gcgtcaggtc aggcgggagc tcctgcaggt ttacctcgca tagacgggtc agggcgcggg   8700
ctagatccag gtgataccta atttccaggg gctggttggt ggcggcgtcg atggcttgca   8760
agaggccgca tccccgcggc gcgactacgg taccgcgcgg cgggcggtgg gccgcggggg   8820
tgtccttgga tgatgcatct aaaagcggtg acgcgggcga gccccggag gtagggggg    8880
ctccggaccc gccgggagag ggggcagggg cacgtcggcg ccgcgcgcgg gcaggagctg   8940
gtgctgcgcg cgtaggttgc tggcgaacgc gacgacgcgg cggttgatct cctgaatctg   9000
gcgcctctgc gtgaagacga cgggcccggt gagcttgagc ctgaaagaga gttcgacaga   9060
atcaatttcg gtgtcgttga cggcggcctg gcgcaaaatc tcctgcacgt ctcctgagtt   9120
gtcttgatag gcgatctcgg ccatgaactg ctcgatctct tcctcctgga gatctccgcg   9180
tccggctcgc tccacggtgg cggcgaggtc gttggaaatg cgggccatga gctgcgagaa   9240
ggcgttgagg cctccctcgt tccagacgcg gctgtagacc acgccccctt cggcatcgcg   9300
ggcgcgcatg accacctgcg cgagattgag ctccacgtgc cgggcgaaga cggcgtagtt   9360
tcgcaggcgc tgaaagaggt agttgagggt ggtggcggtg tgttctgcca cgaagaagta   9420
cataacccag cgtcgcaacg tggattcgtt gatatccccc aaggcctcaa ggcgctccat   9480
ggcctcgtag aagtccacgg cgaagttgaa aaactgggag ttgcgcgccg acacggttaa   9540
ctcctcctcc agaagacgga tgagctcggc gacagtgtcg cgcacctcgc gctcaaaggc   9600
tacagggggcc tcttcttctt cttcaatctc ctcttccata agggcctccc cttcttcttc   9660
ttctggcggc ggtgggggag gggggacacg gcggcgacga cggcgcaccg ggaggcggtc   9720
gacaaagcgc tcgatcatct ccccgcgcg acggcgcatg gtctcggtga cggcgcggcc   9780
gttctcgcgg gggcgcagtt ggaagacgcc gcccgtcatg tcccggttat gggttggcgg   9840
ggggctgcca tgcggcaggg atacggcgct aacgatgcat ctcaacaatt gttgtgtagg   9900
tactccgccg ccgagggacc tgagcgagtc cgcatcgacc ggatcggaaa acctctcgag   9960
aaaggcgtct aaccagtcac agtcgcaagg taggctgagc accgtggcgg gcggcagcgg  10020
gcggcggtcg gggttgtttc tggcggaggt gctgctgatg atgtaattaa agtaggcggt  10080
cttgagacgg cggatggtcg acagaagcac catgtccttg ggtccggcct gctgaatgcg  10140
caggcggtcg gccatgcccc aggcttcgtt ttgacatcgg cgcaggtctt tgtagtagtc  10200
ttgcatgagc ctttctaccg gcacttcttc ttctccttcc tcttgtcctg catctcttgc  10260
atctatcgct gcggcggcgg cggagtttgg ccgtaggtgg cgccctcttc ctcccatgcg  10320
tgtgaccccg aagcccctca tcggctgaag cagggctagg tcggcgacaa cgcgctcggc  10380
taatatggcc tgctgcacct gcgtgagggt agactggaag tcatccatgt ccacaaagcg  10440
gtggtatgcg cccgtgttga tggtgtaagt gcagttggcc ataacggacc agttaacggt  10500
ctggtgaccc ggctgcgaga gctcggtgta cctgagacgc gagtaagccc tcgagtcaaa  10560
tacgtagtcg ttgcaagtcc gcaccaggta ctggtatccc accaaaaagt gcggcggcgg  10620
ctggcggtag aggggccagc gtagggtggc cggggctccg ggggcgagat cttccaacat  10680
aaggcgatga tatccgtaga tgtacctgga catccaggtg atgccggcgg cggtggtgga  10740
ggcgcgcgga aagtcgcgga cgcggttcca gatgttgcgc agcggcaaaa agtgctccat  10800
ggtcgggacg ctctggccgg tcaggcgcgc gcaatcgttg acgctctaga ccgtgcaaaa  10860
```

```
ggagagcctg taagcgggca ctcttccgtg gtctggtgga taaattcgca agggtatcat    10920
ggcggacgac cggggttcga gccccgtatc cggccgtccg ccgtgatcca tgcggttacc    10980
gcccgcgtgt cgaacccagg tgtgcgacgt cagacaacgg gggagtgctc cttttggctt    11040
ccttccaggc gcggcggctg ctgcgctagc tttttggcc actggccgcg cgcagcgtaa     11100
gcggttaggc tggaaagcga aagcattaag tggctcgctc cctgtagccg gagggttatt    11160
ttccaagggt tgagtcgcgg gaccccggt tcgagtctcg gaccggccgg actgcggcga     11220
acggggtttt gcctccccgt catgcaagac cccgcttgca aattcctccg gaaacaggga    11280
cgagcccctt ttttgctttt cccagatgca tccggtgctg cggcagatgc gccccctcc    11340 tcagcagcgg caagagcaag agcagcggca gacatgcagg gcaccctccc ctcctcctac    11400
cgcgtcagga ggggcgacat ccgcggttga cgcggcagca gatggtgatt acgaaccccc    11460
gcggcgccgg gcccggcact acctggactt ggaggagggc gagggcctgg cgcggctagg    11520
agcgccctct cctgagcgt acccaagggt gcagctgaag cgtgatacgc gtgaggcgta     11580
cgtgccgcgg cagaacctgt ttcgcgaccg cgagggagag gagcccgagg agatgcggga    11640
tcgaaagttc cacgcagggc gcgagctgcg gcatggcctg aatcgcgagc ggttgctgcg    11700
cgaggaggac tttgagcccg acgcgcgaac cgggattagt cccgcgcgcg cacacgtggc    11760
ggccgccgac ctggtaaccg catacgagca gacggtgaac caggagatta actttcaaaa    11820
aagctttaac aaccacgtgc gtacgcttgt ggcgcgcgag gaggtggcta taggactgat    11880
gcatctgtgg gactttgtaa gcgcgctgga gcaaaaccca aatagcaagc cgctcatggc    11940
gcagctgttc cttatagtgc agcacagcag ggacaacgag gcattcaggg atgcgctgct    12000
aaacatagta gagcccgagg gccgctggct gctcgatttg ataaacatcc tgcagagcat    12060
agtggtgcag gagcgcagct tgagcctggc tgacaaggtg gccgccatca actattccat    12120
gcttagcctg ggcaagtttt acgcccgcaa gatataccat accccttacg ttcccataga    12180
caaggaggta aagatcgagg ggttctacat gcgcatggcg ctgaaggtgc ttaccttgag    12240
cgacgacctg ggcgttatc gcaacgagcg catccacaag gccgtgagcg tgagccggcg    12300
gcgcgagctc agcgaccgcg agctgatgca cagcctgcaa agggccctgg ctggcacggg    12360
cagcggcgat agagaggccg agtcctactt tgacgcgggc gctgacctgc gctgggcccc    12420
aagccgacgc gccctggagg cagctggggc cggacctggg ctggcggtgg cacccgcgcg    12480
cgctggcaac gtcggcggcg tggaggaata tgacgaggac gatgagtacg agccagagga    12540
cggcgagtac taagcggtga tgtttctgat cagatgatgc aagacgcaac ggacccggcg    12600
gtgcgggcgg cgctgcagag ccagccgtcc ggccttaact ccacggacga ctggcgccag    12660
gtcatggacc gcatcatgtc gctgactgcg cgcaatcctg acgcgttccg gcagcagccg    12720
caggccaacc ggctctccgc aattctggaa gcggtggtcc cggcgcgcgc aaaccccacg    12780
cacgagaagg tgctggcgat cgtaaacgcg ctggccgaaa acagggccat ccggcccgac    12840
gaggccggcc tggtctacga cgcgctgctt cagcgcgtgg ctcgttacaa cagcggcaac    12900
gtgcagacca acctggaccg gctggtgggg gatgtgcgcg aggccgtggc gcagcgtgag    12960
cgcgcgcagc agcagggcaa cctgggctcc atggttgcac taaacgcctt cctgagtaca    13020 cagccccgcca acgtgccgcg gggacaggag gactacacca actttgtgag cgcactgcgg    13080
ctaatggtga ctgagacacc gcaaagtgag gtgtaccagt ctgggccaga ctatttttc     13140 cagaccagta gacaaggcct gcagaccgta aacctgagcc aggctttcaa aaacttgcag    13200
gggctgtggg gggtgcgggc tcccacaggc gaccgcgcga ccgtgtctag cttgctgacg    13260
```

```
cccaactcgc gcctgttgct gctgctaata gcgcccttca cggacagtgg cagcgtgtcc   13320
cgggacacat acctaggtca cttgctgaca ctgtaccgcg aggccatagg tcaggcgcat   13380
gtggacgagc atactttcca ggagattaca agtgtcagcc gcgcgctggg gcaggaggac   13440
acgggcagcc tggaggcaac cctaaactac ctgctgacca accggcggca aagatcccc    13500 tcgttgcaca gtttaaacag cgaggaggag cgcattttgc gctacgtgca gcagagcgtg   13560
agccttaacc tgatgcgcga cggggtaacg cccagcgtgg cgctggacat gaccgcgcgc   13620
aacatggaac cgggcatgta tgcctcaaac cggccgttta tcaaccgcct aatggactac   13680
ttgcatcgcg cggccgccgt gaaccccgag tatttcacca atgccatctt gaacccgcac   13740
tggctaccgc cccctggttt ctacaccggg ggattcgagg tgcccgaggg taacgatgga   13800
ttcctctggg acgacataga cgacagcgtg ttttccccgc aaccgcagac cctgctagag   13860
ttgcaacagc gcgagcaggc agaggcggcg ctgcgaaagg aaagcttccg caggccaagc   13920
agcttgtccg atctaggcgc tgcggccccg cggtcagatg ctagtagccc atttccaagc   13980
ttgatagggt ctcttaccag cactcgcacc acccgcccgc gcctgctggg cgaggaggag   14040
tacctaaaca actcgctgct gcagccgcag cgcgaaaaaa acctgcctcc ggcatttccc   14100
aacaacggga tagagagcct agtggacaag atgagtagat ggaagacgta cgcgcaggag   14160
cacagggacg tgccaggccc gcgcccgccc accgtcgtc aaaggcacga ccgtcagcgg    14220
ggtctggtgt gggaggacga tgactcggca gacgacagca gcgtcctgga tttgggaggg   14280
agtggcaacc cgtttgcgca ccttcgcccc aggctgggga gaatgttta aaaaaaaaa    14340 agcatgatgc aaaataaaaa actcaccaag gccatggcac cgagcgttgg ttttcttgta   14400 ttcccttag tatgcggcgc gcggcgatgt atgaggaagg tcctcctccc tcctacgaga    14460
gtgtggtgag cgcggcgcca gtggcggcgg cgctgggttc tcccttcgat gctccctgg    14520 acccgccgtt tgtgcctccg cggtacctgc ggcctaccgg ggggagaaac agcatccgtt   14580
actctgagtt ggcaccccta ttcgacacca cccgtgtgta cctggtggac aacaagtcaa   14640
cggatgtggc atccctgaac taccagaacg accacagcaa ctttctgacc acggtcattc   14700
aaaacaatga ctacagcccg ggggaggcaa gcacacagac catcaatctt gacgaccggt   14760
cgcactgggg cggcgacctg aaaaccatcc tgcataccaa catgccaaat gtgaacgagt   14820
tcatgtttac caataagttt aaggcgcggg tgatggtgtc gcgcttgcct actaaggaca   14880
atcaggtgga gctgaaatac gagtgggtgg agttcacgct gcccgagggc aactactccg   14940
agaccatgac catagacctt atgaacaacg cgatcgtgga gcactacttg aaagtgggca   15000
gacagaacgg ggttctggaa agcgacatcg gggtaaagtt tgacacccgc aacttcagac   15060
tggggtttga ccccgtcact ggtcttgtca tgcctggggt atatacaaac gaagccttcc   15120
atccagacat cattttgctg ccaggatgcg gggtggactt cacccacagc cgcctgagca   15180
acttgttggg catccgcaag cggcaaccct tccaggaggg ctttaggatc acctacgatg   15240
atctggaggg tggtaacatt cccgcactgt tggatgtgga cgcctaccag gcgagcttga   15300
aagatgacac cgaacagggc gggggtggcg caggcggcag caacagcagt ggcagcggcg   15360
cggaagagaa ctccaacgcg gcagccgcgg caatgcagcc ggtggaggac atgaacgatc   15420
atgccattcg cggcgacacc tttgccacac gggctgagga gaagcgcgct gaggccgaag   15480
cagcggccga agctgccgcc cccgctgcgc aacccgaggt cgagaagcct cagaagaaac   15540
cggtgatcaa ccccctgaca gaggacagca agaaacgcag ttacaaccta ataagcaatg   15600
acagcacctt cacccagtac cgcagctggt accttgcata caactacggc gaccctcaga   15660
```

```
ccggaatccg ctcatggacc ctgctttgca ctcctgacgt aacctgcggc tcggagcagg   15720
tctactggtc gttgccagac atgatgcaag accccgtgac cttccgctcc acgcgccaga   15780
tcagcaactt tccggtggtg ggcgccgagc tgttgcccgt gcactccaag agcttctaca   15840
acgaccaggc cgtctactcc caactcatcc gccagtttac ctctctgacc cacgtgttca   15900
atcgctttcc cgagaaccag attttggcgc gcccgccagc ccccaccatc accaccgtca   15960
gtgaaaacgt tcctgctctc acagatcacg ggacgctacc gctgcgcaac agcatcggag   16020
gagtccagcg agtgaccatt actgacgcca gacgccgcac ctgccgctac gtttacaagg   16080
ccctgggcat agtctcgccg cgcgtcctat cgagccgcac ttttttgagca agcatgtcca   16140 tccttatatc gcccagcaat aacacaggct ggggcctgcg cttcccaagc aagatgtttg   16200
gcggggccaa gaagcgctcc gaccaacacc cagtgcgcgt gcgcgggcac taccgcgcgc   16260
cctggggcgc gcacaaacgc ggccgcactg ggcgcaccac cgtcgatgac gccatcgacg   16320
cggtggtgga ggaggcgcgc aactacacgc ccacgccgcc accagtgtcc acagtggacg   16380
cggccattca gaccgtggtg cgcggagccc ggcgctatgc taaaatgaag agacggcgga   16440
ggcgcgtagc acgtcgccac cgccgccgac ccggcactgc cgcccaacgc gcggcggcgg   16500
ccctgcttaa ccgcgcacgt cgcaccggcc gacgggcggc catgcgggcc gctcgaaggc   16560
tggccgcggg tattgtcact gtgcccccca ggtccaggcg acgagcggcc gccgcagcag   16620
ccgcggccat tagtgctatg actcagggtc gcaggggcaa cgtgtattgg gtgcgcgact   16680
cggttagcgg cctgcgcgtg cccgtgcgca cccgccccc gcgcaactag attgcaagaa   16740
aaaactactt agactcgtac tgttgtatgt atccagcggc ggcggcgcgc aacgaagcta   16800
tgtccaagcg caaaatcaaa gaagagatgc tccaggtcat cgcgccggag atctatggcc   16860
ccccgaagaa ggaagagcag gattacaagc cccgaaagct aaagcgggtc aaaaagaaaa   16920
agaaagatga tgatgatgaa cttgacgacg aggtggaact gctgcacgct accgcgccca   16980
ggcgacgggt acagtggaaa ggtcgacgcg taaaacgtgt tttgcgaccc ggcaccaccg   17040
tagtctttac gcccggtgag cgctccaccc gcacctacaa gcgcgtgtat gatgaggtgt   17100
acggcgacga ggacctgctt gagcaggcca acgagcgcct cggggagttt gcctacggaa   17160
agcggcataa ggacatgctg gcgttgccgc tggacgaggg caacccaaca cctagcctaa   17220 agccccgtaac actgcagcag gtgctgcccg cgcttgcacc gtccgaagaa aagcgcggcc   17280
taaagcgcga gtctggtgac ttggcaccca ccgtgcagct gatggtaccc aagcgccagc   17340
gactggaaga tgtcttggaa aaaatgaccg tggaacctgg gctggagccc gaggtccgcg   17400
tgcggccaat caagcaggtg gcgccggac tgggcgtgca gaccgtggac gttcagatac   17460
ccactaccag tagcaccagt attgccaccg ccacagaggg catggagaca caaacgtccc   17520
cggttgcctc agcggtggcg gatgccgcg tgcaggcggt cgctgcggcc gcgtccaaga   17580
cctctacgga ggtgcaaacg acccgtggaa tgtttcgcgt ttcagccccc cggcgcccgc   17640
gcggttcgag gaagtacggc gccgccagcc cgctactgcc cgaatatgcc ctacatcctt   17700
ccattgcgcc tacccccggc tatcgtggct acacctaccg ccccagaaga cgagcaacta   17760
cccgacgccg aaccaccact ggaacccgcc gccgccgtcg ccgtcgccag cccgtgctgg   17820
ccccgatttc cgtgcgcagg gtggctcgcg aaggaggcag gacctggtg ctgccaacag   17880 cgcgctacca ccccagcatc gttttaaaagc cggtctttgt ggttcttgca gatatggccc   17940
tcacctgccg cctccgtttc ccggtgccgg gattccgagg aagaatgcac cgtaggaggg   18000
gcatggccgg ccacggcctg acgggcggca tgcgtcgtgc gcaccaccgg cggcggcgcg   18060
```

```
cgtcgcaccg tcgcatgcgc ggcggtatcc tgcccctcct tattccactg atcgccgcgg   18120
cgattggcgc cgtgcccgga attgcatccg tggccttgca ggcgcagaga cactgattaa   18180
aaacaagttg catgtggaaa aatcaaaata aaaagtctgg actctcacgc tcgcttggtc   18240
ctgtaactat tttgtagaat ggaagacatc aactttgcgt ctctggcccc gcgacacggc   18300
tcgcgcccgt tcatgggaaa ctggcaagat atcggcacca gcaatatgag cggtggcgcc   18360
ttcagctggg gctcgctgtg gagcggcatt aaaaatttcg gttccaccgt taagaactat   18420
ggcagcaagg cctggaacag cagcacaggc cagatgctga gggataagtt gaaagagcaa   18480
aatttccaac aaaaggtggt agatggcctg gcctctggca ttagcggggt ggtggacctg   18540
gccaaccagg cagtgcaaaa taagattaac agtaagcttg atcccgcccc tcccgtagag   18600
gagcctccac cggccgtgga gacagtgtct ccagaggggc gtggcgaaaa gcgtccgcgc   18660
cccgacaggg aagaaactct ggtgacgcaa atagacgagc ctccctcgta cgaggaggca   18720
ctaaagcaag gcctgcccac cacccgtccc atcgcgccca tggctaccgg agtgctgggc   18780
cagcacacac ccgtaacgct ggacctgcct cccccgccg acacccagca gaaacctgtg   18840
ctgccaggcc cgaccgccgt tgttgtaacc cgtcctagcc gcgcgtccct gcgccgcgcc   18900
gccagcggtc cgcgatcgtt gcggcccgta ccagtggca actggcaaag cacactgaac   18960
agcatcgtgg gtctgggggt gcaatccctg aagcgccgac gatgcttctg aatagctaac   19020
gtgtcgtatg tgtgtcatgt atgcgtccat gtcgccgcca gaggagctgc tgagccgccg   19080
cgcgcccgct ttccaagatg gctaccccct cgatgatgcc gcagtggtct acatgcaca   19140 tctcgggcca ggacgcctcg gagtacctga gccccgggct ggtgcagttt gcccgcgcca   19200
ccgagacgta cttcagcctg aataacaagt ttagaaaccc cacggtggcg cctacgcacg   19260
acgtgaccac agaccggtcc cagcgtttga cgctgcggtt catccctgtg gaccgtgagg   19320
atactgcgta ctcgtacaag gcgcggttca ccctagctgt gggtgataac cgtgtgctgg   19380
acatggcttc cacgtacttt gacatccgcg gcgtgctgga caggggccct acttttaagc   19440
cctactctgg cactgcctac aacgcccctgg ctcccaaggg tgccccaaat ccttgcgaat   19500
gggatgaagc tgctactgct cttgaaataa acctagaaga agaggacgat gacaacgaag   19560
acgaagtaga cgagcaagct gagcagcaaa aaactcacgt atttgggcag gcgccttatt   19620
ctggtatgaa tattacaaag gagggtattc aaataggtgt cgaaggtcaa acacctaaat   19680
atgccgataa acatttcaa cctgaacctc aaataggaga atctcagtgg tacgaaactg   19740
aaattaatca tgcagctggg agagtcctta aaaagactac cccaatgaaa ccatgttacg   19800
gttcatatgc aaaacccaca aatgaaaatg gagggcaagg cattcttgta aagcaacaaa   19860
atggaaagct agaaagtcaa gtggaaatgc aattttctc aactactgag gcgaccgcag   19920
gcaatggtga taacttgact cctaaagtgg tattgtacag tgaagatgta gatatagaaa   19980
ccccagacac tcatatttct tacatgccca ctattaagga aggtaactca cgagaactaa   20040
tgggccaaca atctatgccc aacaggccta attacattgc ttttagggac aattttattg   20100
gtctaatgta ttacaacagc acgggtaata tgggtgttct ggcgggccaa gcatcgcagt   20160
tgaatgctgt tgtagatttg caagacagaa acacagagct ttcataccag cttttgcttg   20220
attccattgg tgatagaacc aggtacttt ctatgtggaa tcaggctgtt gacagctatg   20280
atccagatgt tagaattatt gaaaatcatg gaactgaaga tgaacttcca aattactgct   20340
ttccactggg aggtgtgatt aatacagaga ctcttaccaa ggtaaaacct aaaacaggtc   20400
aggaaaatgg atgggaaaaa gatgctacag aattttcaga taaaaatgaa ataagagttg   20460
```

```
gaaataattt tgccatggaa atcaatctaa atgccaacct gtggagaaat ttcctgtact   20520
ccaacatagc gctgtatttg cccgacaagc taaagtacag tccttccaac gtaaaaattt   20580
ctgataaccc aaacacctac gactacatga acaagcgagt ggtggctccc gggttagtgg   20640
actgctacat taaccttgga gcacgctggt cccttgacta tatggacaac gtcaaccat    20700 ttaaccacca ccgcaatgct ggcctgcgct accgctcaat gttgctgggc aatggtcgct   20760
atgtgccctt ccacatccag gtgcctcaga agttctttgc cattaaaaac ctccttctcc   20820
tgccgggctc atacacctac gagtggaact tcaggaagga tgttaacatg gttctgcaga   20880
gctccctagg aaatgaccta agggttgacg gagccagcat taagtttgat agcatttgcc   20940
tttacgccac cttcttcccc atggcccaca acaccgcctc cacgcttgag gccatgcttg   21000
aaacgacacc aacgaccagt cctttaacga ctatctctcc gccgccaaca tgctctaccc   21060
tatacccgcc aacgctacca acgtgccat atccatcccc tcccgcaact gggcggcttt    21120
ccgcggctgg gccttcacgc gccttaagac taaggaaacc ccatcactgg gctcgggcta   21180
cgacccttat tacacctact ctggctctat accctaccta gatggaacct tttacctcaa   21240 ccacacctttt aagaaggtgg ccattacctt tgactcttct gtcagctggc ctggcaatga   21300
ccgcctgctt accccaacg agtttgaaat taagcgctca gttgacgggg agggttacaa     21360
cgttgcccag tgtaacatga ccaaagactg gttcctggta caaatgctag ctaactacaa   21420
cattggctac cagggcttct atatcccaga gagctacaag gaccgcatgt actccttctt   21480
tagaaacttc cagcccatga ccgtcaggt ggtggatgat actaaataca aggactacca     21540
acaggtgggc atcctacacc aacacaacaa ctctggattt gttggctacc ttgccccac     21600 catgcgcgaa ggacaggcct accctgctaa cttcccctat ccgcttatag caagaccgc     21660 agttgacagc attacccaga aaaagtttct ttgcgatcgc acccctttggc gcatcccatt   21720 ctccagtaac tttatgtcca tgggcgcact cacagacctg gccaaaaacc ttctctacgc   21780
caactccgcc cacgcgctag acatgacttt tgaggtggat cccatggacg agcccaccct   21840
tctttatgtt ttgttttgaag tctttgacgt ggtccgtgtg caccggccgc accgcggcgt   21900
catcgaaacc gtgtacctgc gcacgccctt ctcggccggc aacgccacaa cataaagaag   21960
caagcaacat caacaacagc tgccgccatg ggctccagtg agcaggaact gaaagccatt   22020
gtcaaagatc ttggttgtgg gccatatttt ttgggcacct atgacaagcg ctttccaggc   22080
tttgtttctc cacacaagct cgcctgcgcc atagtcaata cggccggtcg cgagactggg   22140
ggcgtacact ggatggcctt tgcctggaac ccgcactcaa aaacatgcta cctcttttgag  22200 cccttttggct ttctgacca gcgactcaag caggtttacc agtttgagta cgagtcactc    22260
ctgcgccgta gcgccattgc ttcttccccc gaccgctgta aacgctgga aaagtccacc     22320 caaagcgtac aggggcccaa ctcggccgcc tgtggactat tctgctgcat gtttctccac   22380
gcctttgcca actggcccca aactcccatg gatcacaacc ccaccatgaa ccttattacc   22440
ggggtaccca actccatgct caacagtccc caggtacagc ccaccctgcg tcgcaaccag   22500
gaacagctct acagcttcct ggagcgccac tcgccctact tccgcagcca cagtgcgcag   22560
attaggagcg ccacttcttt ttgtcacttg aaaaacatgt aaaaataatg tactagagac   22620
actttcaata aaggcaaatg cttttatttg tacactctcg ggtgattatt taccccccacc  22680 cttgccgtct gcgccgttta aaaatcaaag gggttctgcc gcgcatcgct atgcgccact   22740
ggcagggaca cgttgcgata ctggtgttta gtgctccact taaactcagg cacaaccatc   22800
cgcggcagct cggtgaagtt ttcactccac aggctgcgca ccatcaccaa cgcgtttagc   22860
```

```
aggtcgggcg ccgatatctt gaagtcgcag ttggggcctc cgccctgcgc gcgcgagttg   22920
cgatacacag ggttgcagca ctggaacact atcagcgccg ggtggtgcac gctggccagc   22980
acgctcttgt cggagatcag atccgcgtcc aggtcctccg cgttgctcag ggcgaacgga   23040
gtcaactttg gtagctgcct tcccaaaaag ggcgcgtgcc caggctttga gttgcactcg   23100
caccgtagtg gcatcaaaag gtgaccgtgc ccggtctggg cgttaggata cagcgcctgc   23160
ataaaagcct tgatctgctt aaaagccacc tgagcctttg cgccttcaga gaagaacatg   23220
ccgcaagact tgccggaaaa ctgattggcc ggacaggccg cgtcgtgcac gcagcacctt   23280
gcgtcggtgt tggagatctg caccacattt cggcccacc ggttcttcac gatcttggcc    23340
ttgctagact gctccttcag cgcgcgctgc ccgttttcgc tcgtcacatc catttcaatc   23400
acgtgctcct tatttatcat aatgcttccg tgtagacact taagctcgcc ttcgatctca   23460
gcgcagcggt gcagccacaa cgcgcagccc gtgggctcgt gatgcttgta ggtcacctct   23520
gcaaacgact gcaggtacgc ctgcaggaat cgccccatca tcgtcacaaa ggtcttgttg   23580
ctggtgaagg tcagctgcaa cccgcggtgc tcctcgttca gccaggtctt gcatacggcc   23640
gccagagctt ccacttggtc aggcagtagt ttgaagttcg cctttagatc gttatccacg   23700
tggtacttgt ccatcagcgc gcgcgcagcc tccatgccct tctcccacgc agacacgatc   23760
ggcacactca gcgggttcat caccgtaatt tcactttccg cttcgctggg ctcttcctct   23820
tcctcttgcg tccgcatacc acgcgccact gggtcgtctt cattcagccg ccgcactgtg   23880
cgcttacctc ctttgccatg cttgattagc accggtgggt tgctgaaacc caccatttgt   23940
agcgccacat cttctctttc ttcctcgctg tccacgatta cctctggtga tggcgggcgc   24000
tcgggcttgg gagaagggcg cttcttttc ttccttgggcg caatggccaa atccgccgcc    24060
gaggtcgatg gccgcgggct gggtgtgcgc ggcaccagcg cgtcttgtga tgagtcttcc   24120
tcgtcctcgg actcgatacg ccgcctcatc cgctttttg ggggcgcccg gggaggcggc    24180
ggcgacgggg acgggacga cacgtcctcc atggttgggg gacgtcgcgc cgcaccgcgt    24240
ccgcgctcgg gggtggtttc gcgctgctcc tcttcccgac tggccatttc cttctcctat   24300
aggcagaaaa agatcatgga gtcagtcgag aagaaggaca gcctaaccgc cccctctgag   24360
ttcgccacca ccgcctccac cgatgccgcc aacgcgccta ccaccttccc cgtcgaggca   24420
cccccgcttg aggaggagga agtgattatc gagcaggacc caggttttgt aagcgaagac   24480
gacgaggacc gctcagtacc aacagaggat aaaaagcaag accaggacaa cgcagaggca   24540
aacgaggaac aagtcgggcg gggggacgaa aggcatggcg actacctaga tgtgggagac   24600
gacgtgctgt tgaagcatct gcagcgccag tgcgccatta tctgcgacgc gttgcaagag   24660
cgcagcgatg tgcccctcgc catagcggat gtcagccttg cctacgaacg ccacctattc   24720
tcaccgcgcg tacccccaa acgccaagaa aacggcacat gcgagcccaa cccgcgcctc    24780
aacttctacc ccgtatttgc cgtgccagag gtgcttgcca cctatcacat cttttttccaa   24840 aactgcaaga taccctatc ctgccgtgcc aaccgcagcc gagcggacaa gcagctggcc    24900
ttgcggcagg gcgctgtcat acctgatatc gcctcgctca acgaagtgcc aaaaatcttt   24960
gagggtcttg gacgcgacga gaagcgcgcg gcaaacgctc tgcaacagga aaacagcgaa   25020
aatgaaagtc actctggagt gttggtggaa ctcgagggtg acaacgcgcg cctagccgta   25080
ctaaaacgca gcatcgaggt cacccacttt gcctacccgg cacttaacct accccccaag   25140
gtcatgagca cagtcatgag tgagctgatc gtgcgccgtg cgcagcccct ggagagggat   25200
gcaaatttgc aagaacaaac agaggagggc ctacccgcag ttggcgacga gcagctagcg   25260
```

```
cgctggcttc aaacgcgcga gcctgccgac ttggaggagc gacgcaaact aatgatggcc   25320
gcagtgctcg ttaccgtgga gcttgagtgc atgcagcggt tctttgctga cccggagatg   25380
cagcgcaagc tagaggaaac attgcactac acctttcgac agggctacgt acgccaggcc   25440
tgcaagatct ccaacgtgga gctctgcaac ctggtctcct accttggaat tttgcacgaa   25500
aaccgccttg ggcaaaacgt gcttcattcc acgctcaagg gcgaggcgcg ccgcgactac   25560
gtccgcgact gcgtttactt atttctatgc tacacctggc agacggccat gggcgtttgg   25620
cagcagtgct tggaggagtg caacctcaag gagctgcaga aactgctaaa gcaaaacttg   25680
aaggacctat ggacggcctt caacgagcgc tccgtggccg cgcacctggc ggacatcatt   25740
ttccccgaac gcctgcttaa aaccctgcaa cagggtctgc cagacttcac cagtcaaagc   25800
atgttgcaga actttaggaa ctttatccta gagcgctcag gaatcttgcc cgccacctgc   25860
tgtgcacttc ctagcgactt tgtgcccatt aagtaccgcg aatgccctcc gccgctttgg   25920
ggccactgct accttctgca gctagccaac taccttgcct accactctga cataatggaa   25980
gacgtgagcg gtgacggtct actggagtgt cactgtcgct gcaacctatg caccccgcac   26040
cgctccctgg tttgcaattc gcagctgctt aacgaaagtc aaattatcgg tacctttgag   26100
ctgcagggtc cctcgcctga cgaaaagtcc gcggctccgg ggttgaaact cactccgggg   26160
ctgtggacgt cggcttacct tcgcaaattt gtacctgagg actaccacgc ccacgagatt   26220
aggttctacg aagaccaatc ccgcccgcca aatgcggagc ttaccgcctg cgtcattacc   26280
cagggccaca ttcttggcca attgcaagcc atcaacaaag cccgccaaga gtttctgcta   26340
cgaaagggac gggggggttta cttggacccc cagtccggcg aggagctcaa cccaatcccc   26400
ccgccgccgc agcccatca gcagcagccg cgggccctttg cttcccagga tgcaccccaa   26460
aaagaagctg cagctgccgc cgccacccac ggacgaggag gaatactggg acagtcaggc   26520
agaggaggtt ttggacgagg aggaggagga catgatggaa gactgggaga gcctagacga   26580
ggaagcttcc gaggtcgaag aggtgtcaga cgaaacaccg tcaccctcgg tcgcattccc   26640
ctcgccggcg ccccagaaat cggcaaccgg ttccagcatg gctacaacct ccgctcctca   26700
ggcgccgccg gcactgcccg ttcgccgacc caaccgtaga tgggacacca ctggaaccag   26760
ggccggtaag tccaagcagc cgccgccgtt agcccaagag caacaacagc gccaaggcta   26820
ccgctcatgg cgcgggcaca agaacgccat agttgcttgc ttgcaagact gtggggcaa   26880 catctccttc gcccgccgct tcttctctcta ccatcacggc gtggccttcc cccgtaacat   26940
cctgcattac taccgtcatc tctacagccc atactgcacc ggcggcagcg gcagcggcag   27000
caacagcagc ggccacacag aagcaaaggc gaccggatag caagactctg acaaagccca   27060
agaaatccac agcggcggca gcagcaggag gaggagcgct gcgtctggcg cccaacgaac   27120
ccgtatcgac ccgcgagctt agaaacagga ttttcccac tctgtatgct atatttcaac   27180
agagcagggg ccaagaacaa gagctgaaaa taaaaaacag gtctctgcga tccctcaccc   27240
gcagctgcct gtatcacaaa agcgaagatc agcttcggcg cacgctggaa gacgcggagg   27300
ctctcttcag taaatactgc gcgctgactc ttaaggacta gtttcgcgcc ctttctcaaa   27360
tttaagcgcg aaaactacgt catctccagc ggccacaccc ggcgccagca cctgtcgtca   27420
gcgccattat gagcaaggaa attcccacgc cctacatgtg gagttaccag ccacaaatgg   27480
gacttgcggc tggagctgcc caagactact caacccgaat aaactacatg agcgcgggac   27540
cccacatgat atcccgggtc aacggaatcc gcgcccaccg aaaccgaatt ctcttggaac   27600
aggcggctat taccaccaca cctcgtaata accttaatcc ccgtagttgg cccgctgccc   27660
```

```
tggtgtacca ggaaagtccc gctcccacca ctgtggtact tcccagagac gcccaggccg   27720
aagttcagat gactaactca ggggcgcagc ttgcgggcgg ctttcgtcac agggtgcggt   27780
cgcccgggca gggtataact cacctgacaa tcagagggcg aggtattcag ctcaacgacg   27840
agtcggtgag ctcctcgctt ggtctccgtc cggacgggac atttcagatc ggcggcgccg   27900
gccgctcttc attcacgcct cgtcaggcaa tcctaactct gcagacctcg tcctctgagc   27960
cgcgctctgg aggcattgga actctgcaat ttattgagga gtttgtgcca tcggtctact   28020 ttaaccccctt ctcgggacct cccgccact atccggatca atttattcct aactttgacg   28080
cggtaaagga ctcggcggac ggctacgact gaatgttaag tggagaggca gagcaactgc   28140
gcctgaaaca cctggtccac tgtcgccgcc acaagtgctt tgcccgcgac tccggtgagt   28200
tttgctactt tgaattgccc gaggatcata tcgagggccc ggcgcacggc gtccggctta   28260
ccgcccaggg agagcttgcc cgtagcctga ttcgggagtt tacccagcgc ccctgctag   28320 ttgagcggga caggggaccc tgtgttctca ctgtgatttg caactgtcct aaccttggat   28380
tacatcaaga tctttgttgc catctctgtg ctgagtataa aaatacaga aattaaaata   28440 tactggggct cctatcgcca tcctgtaaac gccaccgtct tcacccgccc aagcaaacca   28500
aggcgaacct tacctggtac ttttaacatc tctccctctg tgatttacaa cagtttcaac   28560
ccagacggag tgagtctacg agagaacctc tccgagctca gctactccat cagaaaaaac   28620
accaccctcc ttacctgccg ggaacgtacg agtgcgtcac cggccgctgc accacaccta   28680
ccgcctgacc gtaaaccaga cttttttccgg acagacctaa ataactctgt ttaccagaac   28740
aggaggtgag cttagaaaac ccttagggta ttaggccaaa ggcgcagcta ctgtggggtt   28800
tatgaacaat tcaagcaact ctacgggcta ttctaattca ggtttctcta gaatcggggt   28860
tggggttatt ctctgtcttg tgattctctt tattcttata ctaacgcttc tctgcctaag   28920
gctcgccgcc tgctgtgtgc acatttgcat ttattgtcag cttttttaaac gctggggtcg   28980 ccacccaaga taaccatgtg gctgcagagc ctgctgctct tgggcactgt ggcctgcagc   29040
atctctgcac ccgcccgctc gcccagcccc agcacgcagc cctgggagca tgtgaatgcc   29100
atccaggagg cccggcgtct cctgaacctg agtagagaca ctgctgctga gatgaatgaa   29160
acagtagaag tcatctcaga aatgtttgac ctccaggagc cgacctgcct acagacccgc   29220
ctggagctgt acaagcaggg cctgcggggc agcctcacca agctcaaggg ccccttgacc   29280
atgatggcca gccactacaa gcagcactgc cctccaaccc cggaaacttc ctgtgcaacc   29340
cagactatca cctttgaaag tttcaaagag aacctgaagg actttctgct tgtcatcccc   29400
tttgactgct gggagccagt ccaggagtaa tttactaagt tacaaagcta atgtcaccac   29460 taactgctttt acccgctgct tgcaaaacaa attcaaaaag ttagcattat aattagaata   29520
ggatttaaac cccccggtca tttcctgctc aataccattc ccctgaacaa ttgactctat   29580
gtgggatatg ctccagcgct acaaccttga agtcaggctt cctggatgtc agcatctgac   29640
tttggccagc acctgtcccg cggatttgtt ccagtccaac tacagcgacc caccctaaca   29700
gagatgacca acacaaccaa cgcggccgcc gctaccggac ttacatctac cacaaataca   29760
ccccaagttt ctgcctttgt caataactgg gataacttgg gcatgtggtg gttctccata   29820
gcgcttatgt ttgtatgcct tattattatg tggctcatct gctgcctaaa gcgcaaacgc   29880
gcccgaccac ccatctatag tcccatcatt gtgctacacc caaacaatga tggaatccat   29940
agattggacg gactgaaaca catgttcttt tctcttacag tatgattaaa tgagacatga   30000
ttcctcgagt ttttatatta ctgacccttg ttgcgctttt ttgtgcgtgc tccacattgg   30060
```

```
ctgcggtttc tcacatcgaa gtagactgca ttccagcctt cacagtctat ttgctttacg   30120
gatttgtcac cctcacgctc atctgcagcc tcatcactgt ggtcatcgcc tttatccagt   30180
gcattgactg ggtctgtgtg cgctttgcat atctcagaca ccatccccag tacagggaca   30240
ggactatagc tgagcttctt agaattcttt aattatgaaa tttactgtga cttttctgct   30300
gattatttgc accctatctg cgttttgttc cccgacctcc aagcctcaaa gacatatatc   30360
atgcagattc actcgtatat ggaatattcc aagttgctac aatgaaaaaa gcgatctttc   30420
cgaagcctgg ttatatgcaa tcatctctgt tatggtgttc tgcagtacca tcttagccct   30480
agctatatat ccctaccttg acattggctg gaaacgaata gatgccatga accacccaac   30540
tttccccgcg cccgctatgc ttccactgca acaagttgtt gccggcggct ttgtcccagc   30600
caatcagcct cgcccccactt ctcccacccc cactgaaatc agctacttta atctaacagg   30660
aggagatgac tgcaccccta gatctagaaa tggacggaat tattacagag cagcgcctgc   30720
tagaaagacg cagggcagcg gccgagcaac agcgcatgaa tcaagagctc caagacatgg   30780
ttaacttgca ccagtgcaaa aggggtatct tttgtctggt aaagcaggcc aaagtcacct   30840
acgacagtaa taccaccgga caccgcctta gctacaagtt gccaaccaag cgtcagaaat   30900
tggtggtcat ggtgggagaa aagcccatta ccataactca gcactcggta gaaaccgaag   30960
gctgcattca ctcaccttgt caaggacctg aggatctctg cacccttatt aagaccctgt   31020
gcggtctcaa agatcttatt ccctttaact aataaaaaaa aataataaag catcacttac   31080
ttaaaatcag ttagcaaatt tctgtccagt ttattcagca gcacctcctt gccctcctcc   31140
cagctctggt attgcagctt cctcctggct gcaaactttc tccacaatct aaatggaatg   31200
tcagtttcct cctgttcctg tccatccgca cccactatct tcatgttgtt gcagatgaag   31260
cgcgcaagac cgtctgaaga taccttcaac cccgtgtatc catatgacac ggaaaccggt   31320
cctccaactg tgccttttct tactcctccc tttgtatccc ccaatgggtt tcaagagagt   31380 cccccctgggg tactctcttg cgcctatccg aacctctagt tacctccaat ggcatgcttg   31440
cgctcaaaat gggcaacggc ctctctctgg acgaggccgg caaccttacc tcccaaaatg   31500
taaccactgt gagcccacct ctcaaaaaaa ccaagtcaaa cataaacctg gaaatatctg   31560
cacccctcac agttacctca gaagcccccaa ctgtggctgc cgccgcacct ctaatggtcg   31620
cgggcaacac actcaccatg caatcacagg ccccgctaac cgtgcacgac tccaaactta   31680
gcattgccac ccaaggaccc ctcacagtgt cagaaggaaa gctagccctg caaacatcag   31740
gccccctcac caccaccgat agcagtaccc ttactatcac tgcctcaccc cctctaacta   31800
ctgccactgg tagcttgggc attgacttga aagagcccat ttatacacaa aatggaaaac   31860
taggactaaa gtacggggct cctttgcatg taacagacga cctaaacact ttgaccgtag   31920
caactggtcc aggtgtgact attaataata cttccttgca aactaaagtt actggagcct   31980
tgggttttga ttcacaaggc aatatgcaac ttaatgtagc aggaggacta aggattgatt   32040
ctcaaaacag acgccttata cttgatgtta gttatccgtt tgatgctcaa accaactaa   32100 atctaagact aggacagggc cctctttttta taaactcagc ccacaacttg gatattaact   32160
acaacaaagg cctttacttg tttacagctt caaacaattc caaaagctt gaggttaacc   32220 taagcactgc caagggggttg atgtttgacg ctacagccat agccattaat gcaggagatg   32280
ggcttgaatt tggttcacct aatgcaccaa acacaaatcc cctcaaaaca aaaattggcc   32340
atggcctaga atttgattca aacaaggcta tggttcctaa actaggaact ggccttagtt   32400
ttgacagcac aggtgccatt acagtaggaa acaaaaataa tgataagcta actttgtgga   32460
```

```
ccacaccagc tccatctcct aactgtagac taaatgcaga gaaagatgct aaactcactt   32520
tggtcttaac aaaatgtggc agtcaaatac ttgctacagt ttcagttttg gctgttaaag   32580
gcagtttggc tccaatatct ggaacagttc aaagtgctca tcttattata agatttgacg   32640
aaaatggagt gctactaaac aattccttcc tggacccaga atattggaac tttagaaatg   32700
gagatcttac tgaaggcaca gcctatacaa acgctgttgg atttatgcct aacctatcag   32760
cttatccaaa atctcacggt aaaactgcca aaagtaacat tgtcagtcaa gtttacttaa   32820
acggagacaa aactaaacct gtaacactaa ccattacact aaacggtaca caggaaacag   32880
gagacacaac tccaagtgca tactctatgt cattttcatg ggactggtct ggccacaact   32940
acattaatga aatatttgcc acatcctctt cacttttttc atacattgcc caagaataaa   33000
gaatcgtttg tgttatgttt caacgtgttt attttcaat tgcagaaaat ttcaagtcat    33060
ttttcattca gtagtatagc cccaccacca catagcttat acagatcacc gtacttaat    33120 caaactcaca gaaccctagt attcaacctg ccacctccct cccaacacac agagtacaca   33180
gtcctttctc cccggctggc cttaaaaagc atcatatcat gggtaacaga catattctta   33240
ggtgttatat tccacacggt ttcctgtcga gccaaacgct catcagtgat attaataaac   33300
tccccgggca gctcacttaa gttcatgtcg ctgtccagct gctgagccac aggctgctgt   33360
ccaacttgcg gttgcttaac gggcggcgaa ggagaagtcc acgcctacat gggggtagag   33420
tcataatcgt gcatcaggat agggcggtgg tgctgcagca gcgcgcgaat aaactgctgc   33480
cgccgccgct ccgtcctgca ggaatacaac atggcagtgg tctcctcagc gatgattcgc   33540
accgcccgca gcataaggcg ccttgtcctc cgggcacagc agcgcaccct gatctcactt   33600
aaatcagcac agtaactgca gcacagcacc acaatattgt tcaaaatccc acagtgcaag   33660
gcgctgtatc caaagctcat ggcggggacc acagaaccca cgtggccatc ataccacaag   33720
cgcaggtaga ttaagtggcg acccctcata aacacgctgg acataaacat tacctctttt   33780
ggcatgttgt aattcaccac ctcccggtac catataaacc tctgattaaa catggcgcca   33840
tccaccacca tcctaaacca gctggccaaa acctgcccgc cggctataca ctgcagggaa   33900
ccgggactgg aacaatgaca gtggagagcc caggactcgt aaccatggat catcatgctc   33960
gtcatgatat caatgttggc acaacacagg cacacgtgca tacacttcct caggattaca   34020
agctcctccc gcgttagaac catatcccag ggaacaaccc attcctgaat cagcgtaaat   34080
cccacactgc agggaagacc tcgcacgtaa ctcacgttgt gcattgtcaa agtgttacat   34140
tcgggcagca gcggatgatc ctccagtatg gtagcgcggg tttctgtctc aaaaggaggt   34200
agacgatccc tactgtacgg agtgcgccga gacaaccgag atcgtgttgg tcgtagtgtc   34260
atgccaaatg gaacgccgga cgtagtcata tttcctgaag caaaaccagg tgcgggcgtg   34320
acaaacagat ctgcgtctcc ggtctcgccg cttagatcgc tctgtgtagt agttgtagta   34380
tatccactct ctcaaagcat caggcgcccc ctggcttcgg gttctatgta aactccttca   34440
tgcgccgctg ccctgataac atccaccacc gcagaataag ccacacccag ccaacctaca   34500
cattcgttct gcgagtcaca cacgggagga gcgggaagag ctggaagaac catgtttttt   34560
tttttattcc aaaagattat ccaaaacctc aaaatgaaga tctattaagt gaacgcgctc   34620
ccctccggtg gcgtggtcaa actctacagc caaagaacag ataatggcat ttgtaagatg   34680
ttgcacaatg gcttccaaaa ggcaaacggc cctcacgtcc aagtggacgt aaaggctaaa   34740
cccttcaggg tgaatctcct ctataaacat tccagcacct tcaaccatgc ccaaataatt   34800
ctcatctcgc caccttctca atatatctct aagcaaatcc cgaatattaa gtccggccat   34860
```

```
tgtaaaaatc tgctccagag cgccctccac cttcagcctc aagcagcgaa tcatgattgc    34920
aaaaattcag gttcctcaca gacctgtata agattcaaaa gcggaacatt aacaaaaata    34980
ccgcgatccc gtaggtccct tcgcagggcc agctgaacat aatcgtgcag gtctgcacgg    35040
accagcgcgg ccacttcccc gccaggaacc ttgacaaaag aacccacact gattatgaca    35100
cgcatactcg gagctatgct aaccagcgta gccccgatgt aagctttgtt gcatgggcgg    35160
cgatataaaa tgcaaggtgc tgctcaaaaa atcaggcaaa gcctcgcgca aaaagaaag     35220 cacatcgtag tcatgctcat gcagataaag gcaggtaagc tccggaacca ccacagaaaa    35280
agacaccatt tttctctcaa acatgtctgc gggtttctgc ataaacacaa aataaaataa    35340
caaaaaaaca tttaaacatt agaagcctgt cttacaacag gaaaaacaac ccttataagc    35400
ataagacgga ctacggccat gccggcgtga ccgtaaaaaa actggtcacc gtgattaaaa    35460
agcaccaccg acagctcctc ggtcatgtcc ggagtcataa tgtaagactc ggtaaacaca    35520
tcaggttgat tcatcggtca gtgctaaaaa gcgaccgaaa tagcccgggg gaatacatac    35580
ccgcaggcgt agagacaaca ttacagcccc cataggaggt ataacaaaat taataggaga    35640
gaaaaacaca taaacacctg aaaaaccctc ctgcctaggc aaaatagcac cctcccgctc    35700
cagaacaaca tacagcgctt ccacagcggc agccataaca gtcagcctta ccagtaaaaa    35760
agaaaaccta ttaaaaaaac accactcgac acggcaccag ctcaatcagt cacagtgtaa    35820
aaaagggcca agtgcagagc gagtatatat aggactaaaa aatgacgtaa cggttaaagt    35880
ccacaaaaaa cacccagaaa accgcacgcg aacctacgcc cagaaacgaa agccaaaaaa    35940
cccacaactt cctcaaatcg tcacttccgt tttcccacgt tacgtcactt cccatttaa     36000 ttaagaaaac tacaattccc aacacataca agttactccg ccctaaaacc tacgtcaccc    36060
gccccgttcc cacgccccgc gccacgtcac aaactccacc ccctcattat catattggct    36120
tcaatccaaa ataaggtata ttattgatga tg                                   36152
```

<210> SEQ ID NO 4
<211> LENGTH: 582
<212> TYPE: DNA
<213> ORGANISM: Artificial Sequence
<220> FEATURE:
<223> OTHER INFORMATION: Recombinant immune regulatory element GM-CSF in
      membrane-bound form (mbGM-CSF)

<400> SEQUENCE: 4

```
atgtggctgc agagcctgct gctcttgggc actgtggcct gcagcatctc tgcacccgcc     60
cgctcgccca gccccagcac gcagccctgg gagcatgtga atgccatcca ggaggcccgg    120
cgtctcctga acctgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaagcagc actgccctcc aacccccgaa acttcctgtg caacccagac tatcacctttt   360 gaaagtttca agagaacctt gaaggactttt ctgcttgtca tccccttga ctgctgggag    420 ccagtccagg aggctgtggg ccaggacacg caggaggtca tcgtggtgcc acactccttg    480
ccctttaagg tggtggtgat ctcagccatc ctggccctgg tggtgctcac catcatctcc    540
cttatcatcc tcatcatgct ttggcagaag aagccacgtt ag                       582
```

<210> SEQ ID NO 5
<211> LENGTH: 1772
<212> TYPE: DNA

<213> ORGANISM: Artificial Sequence
<220> FEATURE:
<223> OTHER INFORMATION: Chimeric fiber protein sequence in the genome
of recombinant KH-904, in which the fiber knob of the fiber gene
is from serotype 35 of human adenovirus

<400> SEQUENCE: 5

```
atgaagcgcg caagaccgtc tgaagatacc ttcaacccg tgtatcctat gacacggaaa      60
ccggtcctcc aactgtgcct tttcttactc ctcccttgt atccccaat gggtttcaag      120
agagtccccc tggggtactc tctttgcgcc tatccgaacc tctagttacc tccaatggca    180
tgcttgcgct caaatgggc aacgcctct ctctggacga ggccggcaac cttacctccc      240
aaaatgtaac cactgtgagc ccacctctca aaaaaccaa gtcaaacata aacctggaaa    300
tatctgcacc cctcacagtt acctcagaag ccctaactgt ggctgccgcc gcacctctaa   360
tggtcgcggg caacacactc accatgcaat cacaggcccc gctaaccgtg cacgactcca   420
aacttagcat tgccacccaa ggaccctca cagtgtcaga aggaaagcta gccctgcaaa    480
catcaggccc cctcaccacc accgatagca gtaccttac tatcactgcc tcacccctc   540
taactactgc cactggtagc ttgggcattg acttgaaaga gcccatttat acacaaaatg   600
gaaaactagg actaaagtac ggggctcctt tgcatgtaac agacgaccta aacactttga   660
ccgtagcaac tggtccaggt gtgactatta ataatacttc cttgcaaact aaagttactg   720
gagccttggg ttttgattca caaggcaata tgcaacttaa tgtagcagga ggactaagga   780
ttgattctca aaacagacgc cttatacttg atgttagtta tccgtttgat gctcaaaacc   840
aactaaatct aagactagga cagggccctc tttttataaa ctcagcccac aacttggata   900
ttaactacaa caaaggcctt tacttgttta cagcttcaaa caattccaaa agcttgagg    960
ttaacctaag cactgccaag gggttgatgt ttgacgctac agccatagcc attaatgcag  1020
gagatgggct tgaattggt tcacctaatg caccaaacac aaatcccctc aaaacaaaaa  1080
ttggccatgg cctagaattt gattcaaaca aggctatggt tcctaaacta ggaactggcc  1140
ttagttttga cagcacaggt gccattacag taggaaacaa aaataatgat aagctaacct  1200
tatggactgg aataaaccct ccacctaact gtcaaattgt ggaaaacact aatacaaatg  1260
atggcaaact tactttagta ttagtaaaaa atggagggct tgttaatggc tacgtgtctc  1320
tagttggtgt atcagacact gtgaaccaaa tgttcacaca aaagacagca aacatccaat  1380
taagattata ttttgactct tctggaaatc tattaactga ggaatcagac ttaaaaattc  1440
cacttaaaaa taaatcttct acagcgacca gtgaaactgt agccagcagc aaagccttta  1500
tgccaagtac tacagcttat cccttcaaca ccactactag ggatagtgaa aactacattc  1560
atggaatatg ttactacatg actagttatg atagaagtct attcccttg aacatttcta   1620
taatgctaaa cagccgtatg atttcttcca atgttgccta tgccatacaa tttgaatgga  1680
atctaaatgc aagtgaatct ccagaaagca acatagctac gctgaccaca tcccccttt   1740
tcttttctta cattacagaa gacgacaact aa                                 1772
```

What is claimed is:

1. An adenovirus comprising the hTERT promoter as shown in SEQ ID NO:2 and an immune regulatory gene, wherein the adenovirus optionally comprises an enhancer, silencer, or a combination thereof.

2. The adenovirus of claim 1, wherein the adenovirus is selected from the group consisting of adenovirus serotypes: Ad2, Ad5, Ad35, and Ad41.

3. The adenovirus of claim 1, wherein the adenovirus comprises E1A and E1B genes that are linked by an internal ribosome entry site (IRES).

4. The adenovirus of claim 1, wherein the adenovirus is an adenovirus serotype 5 comprising the fiber knob of adenovirus serotype 35 in place of the adenovirus serotype 5 fiber knob.

5. The adenovirus of claim 1, wherein the adenovirus comprises a transcription terminal element inserted downstream of the inverted terminal repeat (ITR) and the packaging site and upstream of a heterologous promoter.

6. The adenovirus of claim 1, wherein the adenovirus comprises a deletion of the 10.4K, 14.5K, and 14.7K coding sequences in the E3 region of said adenovirus.

7. The adenovirus of claim 1, wherein the adenovirus is an adenovirus serotype 5 comprising E1A and E1B genes that are linked by an IRES and the adenovirus further comprising a transcription terminal element inserted downstream of the ITR and the packaging site and upstream of a heterologous promoter, wherein the serotype 5 fiber knob is replaced by the fiber knob of adenovirus serotype 35.

8. The adenovirus of claim 5, wherein said transcription terminal element is the SV40 early poly(A) signal sequence.

9. The adenovirus of claim 1, wherein the immune regulatory gene is a gene encoding a protein that improves a human immune response selected from the group consisting of genes that encode IL-2, IL-10, IL-12, IL-15, IL-24, IL-25, GM-CSF, G-CSF, INF-alpha, and INF-beta.

10. The adenovirus of claim 9, wherein the gene encoding a protein that improves a human immune response is GM-CSF.

11. The adenovirus of claim 10, wherein said GM-CSF is a membrane bound form of GM-CSF.

12. The adenovirus of claim 1, wherein the adenovirus is an adenovirus serotype 5 comprising E1A and E1B genes that are linked by an IRES and the adenovirus further comprises a transcription terminal element inserted downstream of the ITR and the packaging site and upstream of a heterologous promoter, wherein the serotype 5 fiber knob is replaced by the fiber knob of adenovirus serotype 35, wherein the immune regulatory gene is the GM-CSF gene.

13. The adenovirus of claim 1, wherein the adenovirus comprises the sequence shown in SEQ ID NO:3.

14. The adenovirus of claim 1, wherein the adenovirus is an adenovirus serotype 5, wherein the serotype 5 fiber knob is replaced by the fiber knob of adenovirus serotype 35, wherein the immune regulatory gene is the GM-CSF gene.

15. The adenovirus of claim 1, wherein the adenovirus comprises a transcription terminal element inserted downstream of the ITR and the packaging site and upstream of a heterologous promoter and comprises a deletion of the 10.4K, 14.5K, and 14.7K coding sequences in the E3 region of said adenovirus, wherein the immune regulatory gene is the GM-CSF gene.

16. The adenovirus of claim 12, wherein said GM-CSF is a membrane bound form of GM-CSF.

17. A promoter having the sequence as shown in SEQ ID NO: 2.

18. A pharmaceutical composition comprising the adenovirus of claim 1.

19. The pharmaceutical composition of claim 18, wherein it is formulated for injection application.

20. The pharmaceutical composition of claim 18, wherein the composition is applied together with chemotherapy and radiotherapy.

* * * * *